US007899507B2

(12) United States Patent
Al-Ali et al.

(10) Patent No.: US 7,899,507 B2
(45) Date of Patent: Mar. 1, 2011

(54) PHYSIOLOGICAL MONITOR

(75) Inventors: Ammar Al-Ali, Costa Mesa, CA (US); Mohamed K. Diab, Mission Viejo, CA (US); Massi E. Kiani, Laguna Niguel, CA (US); Robert James Kopotic, Jamul, CA (US); David Tobler, Westminster, CO (US)

(73) Assignee: MASIMO Corporation, Irvine, CA (US)

( * ) Notice: Subject to any disclaimer, the term of this patent is extended or adjusted under 35 U.S.C. 154(b) by 1111 days.

(21) Appl. No.: 11/417,545

(22) Filed: May 3, 2006

(65) Prior Publication Data

US 2006/0270920 A1 Nov. 30, 2006

Related U.S. Application Data

(63) Continuation of application No. 11/104,720, filed on Apr. 13, 2005, which is a continuation of application No. 10/668,487, filed on Sep. 22, 2003, now Pat. No. 6,898,452, which is a continuation of application No. 10/026,013, filed on Dec. 21, 2001, now Pat. No. 6,714,804, which is a continuation of application No. 09/323,176, filed on May 27, 1999, now Pat. No. 6,334,065.

(60) Provisional application No. 60/087,802, filed on Jun. 3, 1998.

(51) Int. Cl.
*A61B 5/1455* (2006.01)
(52) U.S. Cl. ........................ 600/323; 600/340
(58) Field of Classification Search ................ 600/310, 600/322, 323, 324, 340
See application file for complete search history.

(56) References Cited

U.S. PATENT DOCUMENTS

| 3,704,706 A | 12/1972 | Herczfeld et al. |
| 3,847,483 A | 11/1974 | Shaw et al. |
| 4,109,643 A | 8/1978 | Bond et al. |
| 4,653,498 A | 3/1987 | New, Jr. et al. |
| 4,854,699 A | 8/1989 | Edgar, Jr. |
| 4,869,253 A | 9/1989 | Craig, Jr. et al. |
| 4,911,167 A | 3/1990 | Corenman et al. |
| 4,927,264 A | 5/1990 | Shiga et al. |

(Continued)

FOREIGN PATENT DOCUMENTS

EP 0 555 553 A2 8/1993

(Continued)

OTHER PUBLICATIONS

Bartlett, "Oxygen Kinetics", *Critical Care Physiology*, 13$^{th}$ Ed., pp. 1-23.

(Continued)

*Primary Examiner*—Eric F Winakur
(74) *Attorney, Agent, or Firm*—Knobbe Martens Olson & Bear LLP

(57) ABSTRACT

A patient monitor has multiple sensors adapted to attach to tissue sites of a living subject. The sensors generate sensor signals that are responsive to at least two wavelengths of optical radiation after attenuation by pulsatile blood within the tissue sites. Multiple data channels and associated quality parameters are derived from the sensor signals. A processor is configured to operate on the channels according to the quality parameters so as to provide a robust oxygen status measurement.

11 Claims, 25 Drawing Sheets

U.S. PATENT DOCUMENTS

| | | |
|---|---|---|
| 4,960,128 A | 10/1990 | Gordon et al. |
| 4,964,408 A | 10/1990 | Hink et al. |
| 5,020,516 A | 6/1991 | Biondi et al. |
| 5,041,187 A | 8/1991 | Hink et al. |
| 5,069,213 A | 12/1991 | Polczynski |
| 5,078,136 A | 1/1992 | Stone et al. |
| 5,163,438 A | 11/1992 | Gordon et al. |
| 5,218,962 A * | 6/1993 | Mannheimer et al. ........ 600/331 |
| 5,251,632 A | 10/1993 | Delpy |
| 5,253,645 A | 10/1993 | Friedman et al. |
| 5,273,036 A | 12/1993 | Kronberg et al. |
| 5,308,919 A | 5/1994 | Minnich |
| 5,337,744 A | 8/1994 | Branigan |
| D353,195 S | 12/1994 | Savage et al. |
| D353,196 S | 12/1994 | Savage et al. |
| 5,385,144 A | 1/1995 | Yamanishi et al. |
| 5,396,893 A | 3/1995 | Oberg et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,482,036 A | 1/1996 | Diab et al. |
| 5,490,505 A | 2/1996 | Diab et al. |
| 5,494,043 A | 2/1996 | O'Sullivan et al. |
| 5,522,388 A | 6/1996 | Ishikawa et al. |
| 5,533,511 A | 7/1996 | Kaspari et al. |
| 5,542,421 A | 8/1996 | Erdman |
| 5,562,002 A | 10/1996 | Lalin |
| 5,575,284 A | 11/1996 | Athan et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,647,359 A | 7/1997 | Kohno et al. |
| 5,682,877 A | 11/1997 | Mondry |
| 5,685,299 A | 11/1997 | Diab et al. |
| D393,830 S | 4/1998 | Tobler et al. |
| 5,743,261 A | 4/1998 | Mainiero et al. |
| 5,743,262 A | 4/1998 | Lepper, Jr. et al. |
| 5,743,857 A | 4/1998 | Shinoda et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,827,181 A | 10/1998 | Dias et al. |
| 5,830,131 A | 11/1998 | Caro et al. |
| 5,830,135 A * | 11/1998 | Bosque et al. .............. 600/323 |
| 5,833,618 A | 11/1998 | Caro et al. |
| 5,846,190 A * | 12/1998 | Woehrle ..................... 600/330 |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,954,053 A | 9/1999 | Chance et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,094,592 A | 7/2000 | Yorkey et al. |
| 6,110,522 A | 8/2000 | Lepper, Jr. et al. |
| 6,122,535 A | 9/2000 | Kaestle et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,585 B1 | 4/2004 | Parker |
| 6,725,075 B2 | 4/2004 | Al-Ali |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |

| | | | |
|---|---|---|---|
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Al et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,215,984 B2 | 5/2007 | Diab | |
| 7,489,958 B2 | 2/2009 | Diab | |
| 7,499,741 B2 | 3/2009 | Diab | |
| 7,509,154 B2 | 3/2009 | Diab | |
| 7,530,949 B2 | 5/2009 | Al-Ali | |

FOREIGN PATENT DOCUMENTS

| | | |
|---|---|---|
| EP | 0 807 402 | 11/1997 |
| WO | WO 96/12435 | 5/1996 |

OTHER PUBLICATIONS

Drummond, Willa H., "Ductus Arteriosus", Cardiovascular Disease in the Neonate, pp. 760-771.

Dudell, Glode, et al., "What Constitutes Adequate Oxygenation?" *Pediatrics*, Jan. 1990, pp. 39-41.

Murray, Willie et al., "The Peripheral Pulse Wave: Information Overlooked", *Journal of Clinical Monitoring*, vol. 12, pp. 365-377, Sep. 1996.

Neuhof, H. et al., "Simultaneous Continuous Measurement of Arterial and Mixed Venous Partial $O_2$ Saturation", *The Oxygen Status of Arterial Blood*, Zander, Mertzlufft (eds.), pp. 273-278 (Karger, Basel 1991).

Steinke, John M., Comparison of Mie Theory and the Light Scattering of Red Blood Cells:, *Applied Optics*, vol. 27, No. 19, Oct. 1, 1998, pp. 4027-4033.

Vjayakumar, E., et al., "Pulse Oximetry in Infants of <1500 gm Birth Weight on Supplemental Oxygen: A national Survey", *Journal of Perinatology*, vol. 17, No. 5, 1997, pp. 341-345.

Weis, Carla M. et al., "Oxygen Therapy", Chapt. 46, Pulmonary Disease in the Neonate, pp. 538-545.

White, Katherine, "Completing the Hemodynamic Picture: $Sv_{ox}$", *Heart & Lung*, May 1985, vol. 14, No. 3.

Wolf, Martin, et al., "Continuous Noninvasive Measurement of Cerebral Arterial and Venous Oxygen Saturation at the Bedside in Mechanically Ventilated Noenates\", *Critl Care Med*, 1997, vol. 25, No. 9, pp. 1579-1582.

*Masimo Corporation v. Philips Electronics North America Corporation and Philips Medizin Systeme Böblingen GmbH*, (District of Delaware, Case No. 09-000080(JJF)) Complaint for Patent Infringement dated Feb. 3, 2009, pp. 1-13.

*Masimo Corporation v. Philips Electronics North America Corporation and Philips Medizin Systeme Böblingen GmbH*, (District of Delaware, Case No. 09-00080(JJF)) First Amended Complaint for Patent Infringement dated May 12, 2009, pp. 1-16.

*Masimo Corporation v. Philips Electronics North America Corporation and Philips Medizin Systeme Böblingen GmbH*, (District of Delaware, Case No. 09-00080(JJF)) Defendants' Answer and Philips Electronics North America Corporation's Counterclaims to Masimo's First Amended Complaint dated Jun. 15, 2009, pp. 1-65.

*Masimo Corporation v. Philips Electronics North America Corporation and Philips Medizin Systeme Böblingen GmbH*, (District of Delaware, Case No. 09-00080(JJF)) Masimo's Answer to Philips' Counterclaims dated Jul. 9, 2009, pp. 1-68.

*Masimo Corporation v. Philips Electronics North America Corporation and Philips Medizin Systeme Böblingen GmbH*, (District of Delaware, Case No. 09-00080(JJF)) Defendant/Counterclaim-Plaintiff Philips Electronics North America Corporation Answer to Masimo's Counterclaims dated Aug. 3, 2009, pp. 1-23.

*Masimo Corporation v. Philips Electronics North America Corporation and Philips Medizin Systeme Böblingen GmbH*, (District of Delaware, Case No. 09-00080(JJF)) Defendants' Answer and Philips Electronics North America Corporation's Amended Counterclaims to Masimo's First Amended Complaint, dated Apr. 21, 2010, pp. 1-62.

*Masimo Corporation v. Philips Electronics North America Corporation and Philips Medizin Systeme Böblingen GmbH*, (District of Delaware, Case No. 09-00080(JJF)) Masimo's Answer to Philips' Amended Counterclaims, dated May 10, 2010, pp. 1-76.

*Masimo Corporation v. Philips Electronics North America Corporation and Philips Medizin Systeme Böblingen GmbH*, (District of Delaware, Case No. 09-00080(JJF)) Philips Electronics North America Corporation's Answer to Masimo's Amended Counterclaims (D.I. 102) dated May 27, 2010, pp. 1-24.

*Masimo Corporation v. Philips Electronics North America Corporation and Philips Medizin Systeme Böblingen GmbH*, (District of Delaware, Case No. 09-00080(JJF)) Philips North America Corporation and Philips Medizin Systeme Boblingen GmbH's Seventh Supplemental Objections and Responses to Masimo Corporation's First Set of Interrogatories (Nos. 1-8) dated Jun. 30, 2010, pp. 1-40 (redacted).

Scharf, University of South Florida Department of Anesthesiology, "Pulse Oximetry Through Spectral Analysis," pp. 227-235.

Scharf, USF Department of Anesthesiology, USF Department of Electrical Engineering, Optimization of Portable Pulse Oximetry Through Fourier Analysis, pp. 233-235.

*Mallinckrodt inc. v. Masimo Corp.*, 2004 U.S. Dist. Lexis 28518 (C.D. Cal. Jul. 12, 2004).

*Mallinckrodt, Inc. v. Masimo Corp.*, 147 Fed. Appx. 158, 2005 WL 2139867 (Fed. Cir. 2005).

\* cited by examiner

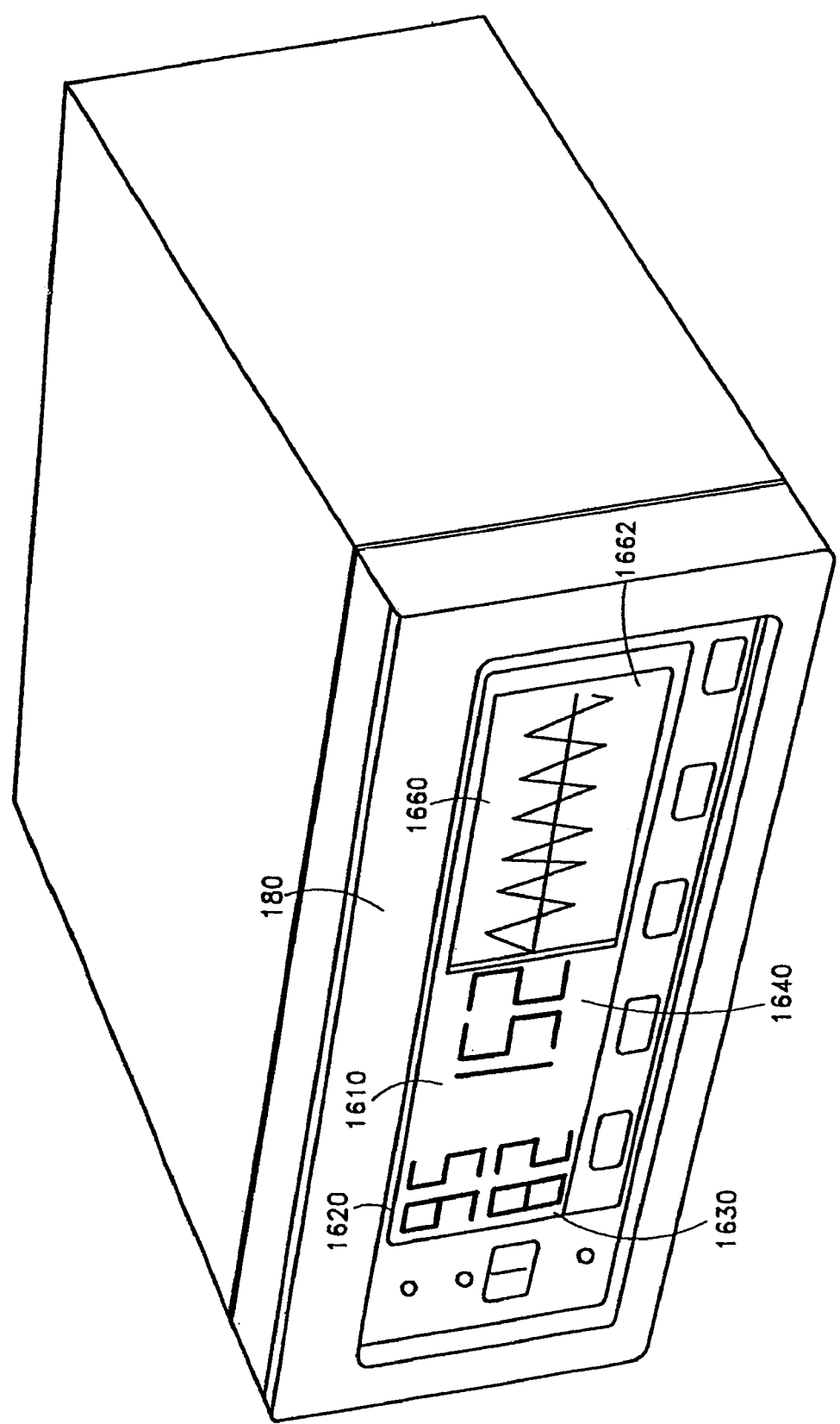

PHYSIOLOGICAL MONITOR

CROSS-REFERENCE TO RELATED APPLICATIONS

This application is a continuation of U.S. application Ser. No. 11/104,720, filed Apr. 13, 2005, which is a continuation of U.S. application Ser. No. 10/668,487, filed Sep. 22, 2003, now U.S. Pat. No. 6,898,452, which is a continuation of U.S. application Ser. No. 10/026,013, filed Dec. 21, 2001, now U.S. Pat. No. 6,714,804, which is a continuation of U.S. application Ser. No. 09/323,176, filed May 27, 1999, now U.S. Pat. No. 6,334,065, which claims priority from U.S. Provisional No. 60/087,802, filed Jun. 3, 1998.

BACKGROUND

The measurement of oxygen delivery to the body and the corresponding oxygen consumption by its organs and tissues is vitally important to medical practitioners in the diagnosis and treatment of various medical conditions. Oxygen delivery, the transport of oxygen from the environment to organs and tissues, depends on the orchestration of several interrelated physiologic systems. Oxygen uptake is determined by the amount of oxygen entering the lung and the adequacy of gas exchange within the lung. This gas exchange is determined by the diffusion of oxygen from the alveolar space to the blood of the pulmonary capillaries. Oxygen is subsequently transported to all organs and tissues by blood circulation maintained by the action of the heart. The availability of oxygen to the organs and tissues is determined both by cardiac output and by the oxygen content in the blood. Oxygen content, in turn, is affected by the concentration of available hemoglobin and hemoglobin oxygen saturation. Oxygen consumption is related to oxygen delivery according to Fick's axiom, which states that oxygen consumption in the peripheral tissues is equal to oxygen delivery via the airway.

Oxygen delivery and oxygen consumption can be estimated from a number of measurable parameters. Because of the diagnostic impracticalities of measuring oxygen uptake and cardiac output, oxygen delivery is typically assessed from the oxygen status of arterial blood alone, such as arterial oxygen partial pressure, $P_aO_2$, and arterial oxygen saturation, $S_aO_2$. $P_aO_2$ represents the relatively small amount of oxygen dissolved in the blood plasma. $S_aO_2$ represents the much larger amount of oxygen chemically bound to the blood hemoglobin. Oxygen consumption is typically assessed from the oxygen status of mixed venous blood, i.e. the oxygen saturation of blood from the pulmonary artery, $S_vO_2$, which is used to estimate the $O_2$ concentration of blood returning from all tissues and organs of the body. These parameters can be measured by both invasive and non-invasive techniques, except $S_vO_2$, which requires an invasive measurement.

Invasive techniques include blood gas analysis using the in vitro measurement of extracted arterial or venous blood, drawn with a syringe and needle or an intervascular catheter. Arterial blood is commonly obtained by puncturing the brachial, radial or femoral artery. Venous blood can be obtained from an arm vein, but such a sample reflects only local conditions. To obtain mixed venous blood, which represents the composite of all venous blood, a long catheter is typically passed through the right heart and into the main pulmonary artery from a peripheral vein. Extracted blood gas analysis utilizes blood gas machines or oximeters. A blood gas machine measures the partial pressure of oxygen, $PO_2$, using a "Clark electrode" that detects the current generated by oxygen diffusing to a sealed platinum electrode across a gas permeable membrane. An oximeter measures the oxygen saturation, $SO_2$, of oxygenated and deoxygenated hemoglobin using spectrophotometry techniques that detect the differential absorption of particular wavelengths of light by these blood components.

Invasive monitoring also includes the in vivo monitoring of blood gas via a catheter sensor inserted into an artery or vein. Miniaturization of the Clark electrode allows placement of the electrode in a catheter for continuous measurement of $PO_2$. A fiber optic equipped catheter attached to an external oximeter allows continuous measurement of oxygen saturation. Because of risks inherent in catheterization and the promotion of blood coagulation by certain sensors, these techniques are typically only used when vitally indicated.

Non-invasive techniques include pulse oximetry, which allows the continuous in vivo measurement of arterial oxygen saturation and pulse rate in conjunction with the generation of a photoplethsymograph waveform. Measurements rely on sensors which are typically placed on the fingertip of an adult or the foot of an infant. Non-invasive techniques also include transcutaneous monitoring of $PO_2$, accomplished with the placement of a heated Clark electrode against the skin surface. These non-invasive oxygen status measurement techniques are described in further detail below.

SUMMARY

Prior art invasive oxygen assessment techniques are inherently limited. Specifically, in vitro measurements, that is, blood extraction and subsequent analysis in a blood gas machine or an oximeter, are non-simultaneous and non-continuous. Further, in vivo measurements through catheterization are not casual procedures and are to be particularly avoided with respect to neonates. Prior art noninvasive techniques are also limited. In particular, conventional pulse oximeters are restricted to measurement of arterial oxygen saturation at a single patient site. Also, transcutaneous monitoring is similarly restricted to the measurement of an estimate of arterial partial pressure at a single patient site, among other limitations discussed further below.

The stereo pulse oximeter according to the present invention overcomes many of the limitations of prior art oxygen status measurements. The word "stereo" comes from the Greek word stereos, which means "solid" or three-dimensional. For example, stereophonic systems use two or more channels to more accurately reproduce sound. The stereo pulse oximeter is similarly multi-dimensional, providing simultaneous, continuous, multiple-site and multiple-parameter oxygen status and plethysmograph (photoplethysmograph) measurements. The stereo pulse oximeter provides a benefit in terms of cost and patient comfort and safety over invasive oxygen status estimation techniques. The multi-dimensional aspects of this invention further provide oxygen status and plethysmograph measurements not available from current noninvasive techniques. In addition, the stereo pulse oximeter allows the isolation of noise artifacts, providing more accurate oxygen status and plethysmograph measurements than available from conventional techniques. The result is improved patient outcome based on a more accurate patient assessment and better management of patient care.

In one aspect of the stereo pulse oximeter, data from a single sensor is processed to advantageously provide continuous and simultaneous multiple-parameter oxygen status and plethysmograph measurements from a particular tissue site. This is in contrast to a conventional pulse oximeter that provides only arterial oxygen saturation data from a tissue site. In particular a physiological monitor comprises a sensor interface and a signal processor. The sensor interface is in communication with a peripheral tissue site and has an output responsive to light transmitted through the site. The signal processor is in communication with the sensor interface output and provides a plurality of parameters corresponding to the oxygen status of the site, the plethysmograph features of the site or both. The parameters comprise a first value and a second value related to the peripheral tissue site. In one embodiment, the first value is an arterial oxygen saturation and the second value is a venous oxygen saturation. In this embodiment, another parameter provided may be the difference between arterial oxygen saturation and venous oxygen saturation at the tissue site. The venous oxygen saturation is derived from an active pulse generated at the site. The signal processor output may further comprise a scattering indicator corresponding to the site, and the sensor interface may further comprise a pulser drive, which is responsive to the scattering indicator to control the amplitude of the active pulse. One of the parameter values may also be an indication of perfusion.

In another aspect of the stereo pulse oximeter, data from multiple sensors is processed to advantageously provide continuous and simultaneous oxygen status measurements from several patient tissue sites. This is in contrast to a conventional pulse oximeter that processes data from a single sensor to provide oxygen status at a single tissue site. In particular, a physiological monitor comprises a plurality of sensor interfaces each in communications with one of a plurality of peripheral tissue sites. Each of the sensor interfaces has one of a plurality of outputs responsive to light transmitted through a corresponding one of the tissue sites. A signal processor is in communication with the sensor interface outputs and has a processor output comprising a plurality of parameters corresponding to the oxygen status of the sites, the plethysmograph features of the sites or both. The parameters may comprise a first value relating to a first of the peripheral tissue sites and a second value relating to a second of the peripheral tissue sites. In one embodiment, the first value and the second value are arterial oxygen saturations. In another embodiment, the first value and the second value are plethysmograph waveform phases. The physiological monitor may further comprise a sensor attachable to each of the tissue sites. This sensor comprises a plurality of emitters and a plurality of detectors, where at least one of the emitters and at least one of the detectors is associated with each of the tissue sites. The sensor also comprises a connector in communications with the sensor interfaces. A plurality of signal paths are attached between the emitters and the detectors at one end of the sensor and the connector at the other end of the sensor.

In yet another aspect of the stereo pulse oximeter, data from multiple sensors is processed to advantageously provide a continuous and simultaneous comparison of the oxygen status between several tissue sites. A conventional oximeter, limited to measurements at a single tissue site, cannot provide these cross-site comparisons. In particular a physiological monitoring method comprises the steps of deriving a reference parameter and a test parameter from oxygen status measured from at least one of a plurality of peripheral tissue sites and comparing that reference parameter to the test parameter so as to determine a patient condition. The reference parameter may be a first oxygen saturation value and the test parameter a second oxygen saturation value. In that case, the comparing step computes a delta oxygen saturation value equal to the arithmetic difference between the first oxygen saturation value and the second oxygen saturation value. In one embodiment, the reference parameter is an arterial oxygen saturation measured at a particular one the tissue sites and the test parameter is a venous oxygen saturation measured at that particular site. In another embodiment, the reference parameter is a first arterial oxygen saturation value at a first of the tissue sites, the test parameter is a second arterial oxygen saturation value at a second of the tissue sites. In yet another embodiment, the reference parameter is a plethysmograph feature measured at a first of the sites, the test parameter is a plethysmograph feature measured at a second of the sites and the monitoring method comparison step determines the phase difference between plethysmographs at the first site and the second site. In a further embodiment, the comparing step determines a relative amount of damping between plethysmographs at the first site and the second site. The multi-dimensional features of these embodiments of the stereo pulse oximeter can be advantageously applied to the diagnosis and managed medical treatment of various medical conditions. Particularly advantageous applications of stereo pulse oximetry include oxygen titration during oxygen therapy, nitric oxide titration during therapy for persistent pulmonary hypertension in neonates (PPHN), detection of a patent ductus arteriosis (PDA), and detection of an aortic coarctation.

BRIEF DESCRIPTION OF THE DRAWINGS

The present invention will be described in detail below in connection with the following drawing figures in which:

FIG. 16A is an illustration of a single-site stereo pulse oximeter display screen;

DETAILED DESCRIPTION

Stereo Pulse Oximetry

Figure 1A:
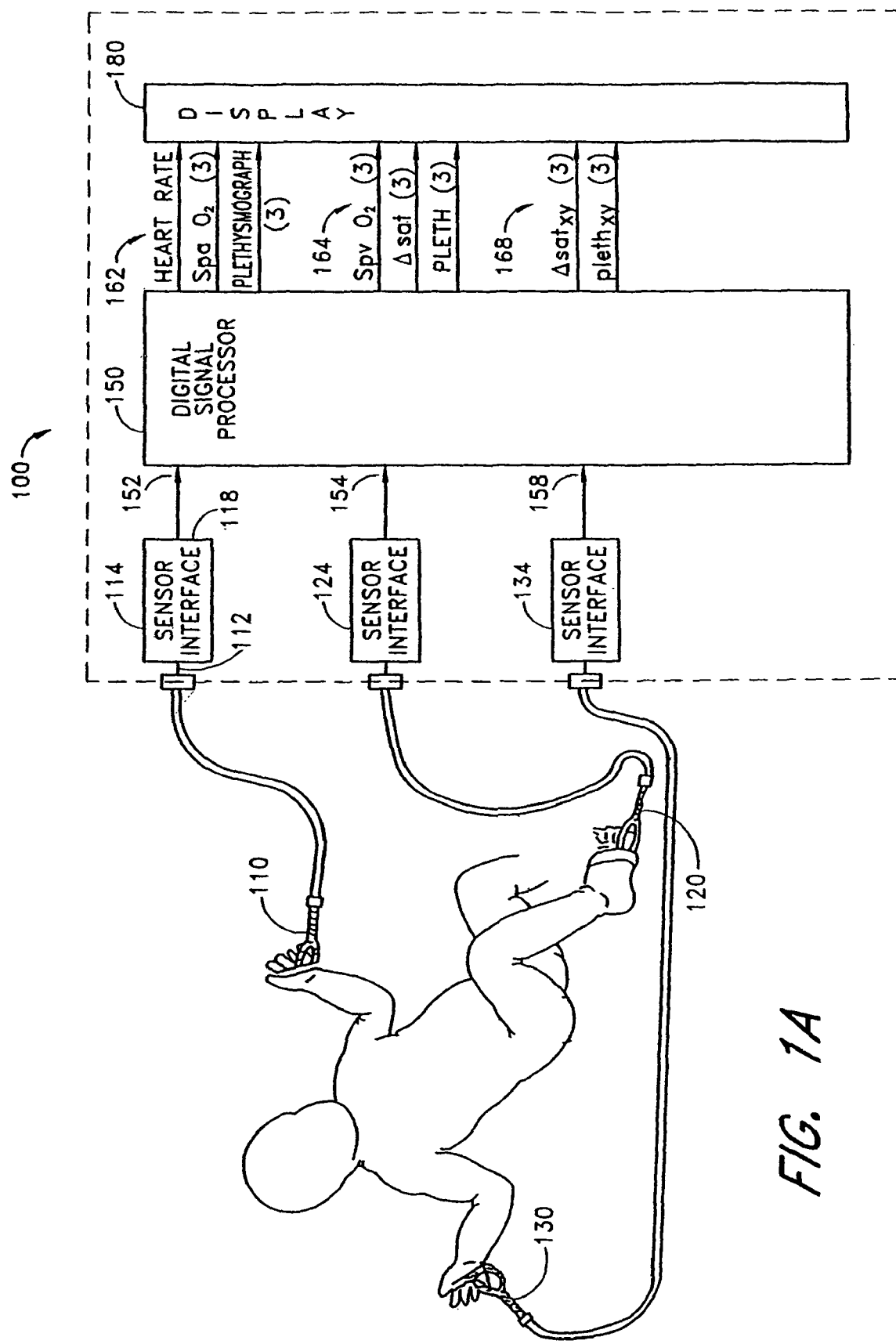
FIG. 1A is a top-level block diagram of a stereo pulse oximeter according to the present invention.

FIG. 1A illustrates the multi-dimensional features of a stereo pulse oximeter 100 according to the present invention. Shown in FIG. 1A is an exemplary stereo pulse oximeter configuration in which a first sensor 110 is attached to a neonate's left hand, a second sensor 120 is attached to one of the neonate's feet, and a third sensor 130 is attached to the neonate's right hand. In general, these sensors are used to obtain oxygen status and photoplethysmograph measurements at peripheral sites, including a person's ears and face, such as the nose and regions of the mouth in addition to hands, feet and limbs, but not including internal sites such as internal organs and the brain.

Each sensor 110, 120, 130 provides a stream of data through a corresponding sensor interface 114, 124, 134 to the digital signal processor (DSP) 150. For example, the first sensor 110 is connected to an input 112 of the first sensor interface 114, and the output 118 of the first sensor interface 114 is attached to a first data channel input 152 of the DSP 150. Similarly, the second sensor 120 provides data to a second data channel input 154 and the third sensor 130 provides data to a third data channel input 158.

Figure 1B:
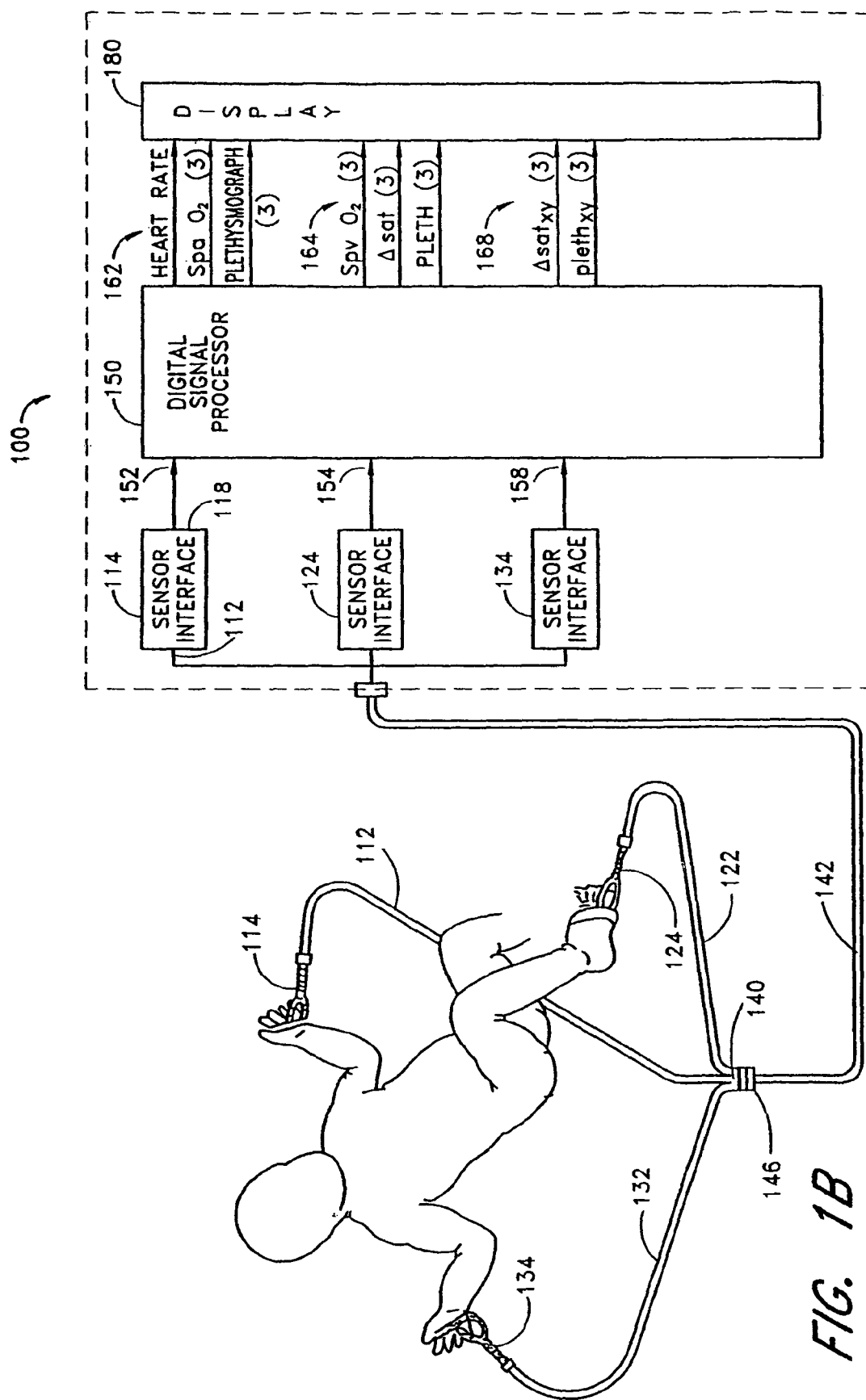
FIG. 1B shows a single-sensor alternative embodiment to FIG. 1A.

FIG. 1B illustrates an alternative embodiment of the separate sensors 110, 120, 130 (FIG. 1A). A stereo sensor 140 has multiple branches 112, 122, 132 each terminating in a sensor portion 114, 124, 134. Each sensor portion 114, 124, 134 has two light emitters and a light detector, as described below, and is attachable to a separate patient site. Thus, the stereo sensor 140 advantageously provides a single sensor device having multiple light emitters and multiple light detectors for attachment to multiple patient tissue sites. A combination of the stereo sensor 140 and a single patient cable 142 advantageously allows a single connection 144 at the stereo pulse oximeter 100 and a single connection 146 at the stereo sensor 140.

The DSP 150 can independently process each data channel input 152, 154, 158 and provide outputs 162 typical of pulse oximetry outputs, such as arterial oxygen saturation, $Sp_aO_2$, the associated plethysmograph waveform and the derived pulse rate. In contrast with a conventional pulse oximeter, however, these outputs 162 include simultaneous measurements at each of several patient tissue sites. That is, for the configuration of FIG. 1A, the stereo pulse oximeter 100 simultaneously displays $Sp_aO_2$ and an associated plethysmograph waveform for three tissue sites in addition to the patient's pulse rate obtained from any one of sites. Further, the DSP 150 can provide unique outputs unavailable from conventional pulse oximeters. These outputs 164 include venous oxygen saturation, $Sp_vO_2$, a comparison of arterial and venous oxygen saturation, $\Delta_{sat}=Sp_{av}O_2=Sp_aO_2-Sp_vO_2$, and pleth, which denotes plethysmograph shape parameters, for each site. In addition, the DSP 150 can provide cross-site outputs that are only available using stereo pulse oximetry. These unique cross-site outputs 168 include $\Delta sat_{xy}=Sp_{ax}O_2-Sp_{ay}O_2$, which denotes the arterial oxygen saturation at site x minus the arterial oxygen saturation at site y. Also included in these outputs 168 is $\Delta pleth_{xy}$, which denotes a comparison of plethysmograph shape parameters measured at site x and site y, as described in detail below. The stereo pulse oximeter also includes a display 180 capable of showing the practitioner the oxygen status and plethysmograph parameters described above. The display 180 has a multiple channel graphical and numerical display capability as described in more detail below.

Pulse Oximetry Sensor

Figure 2:
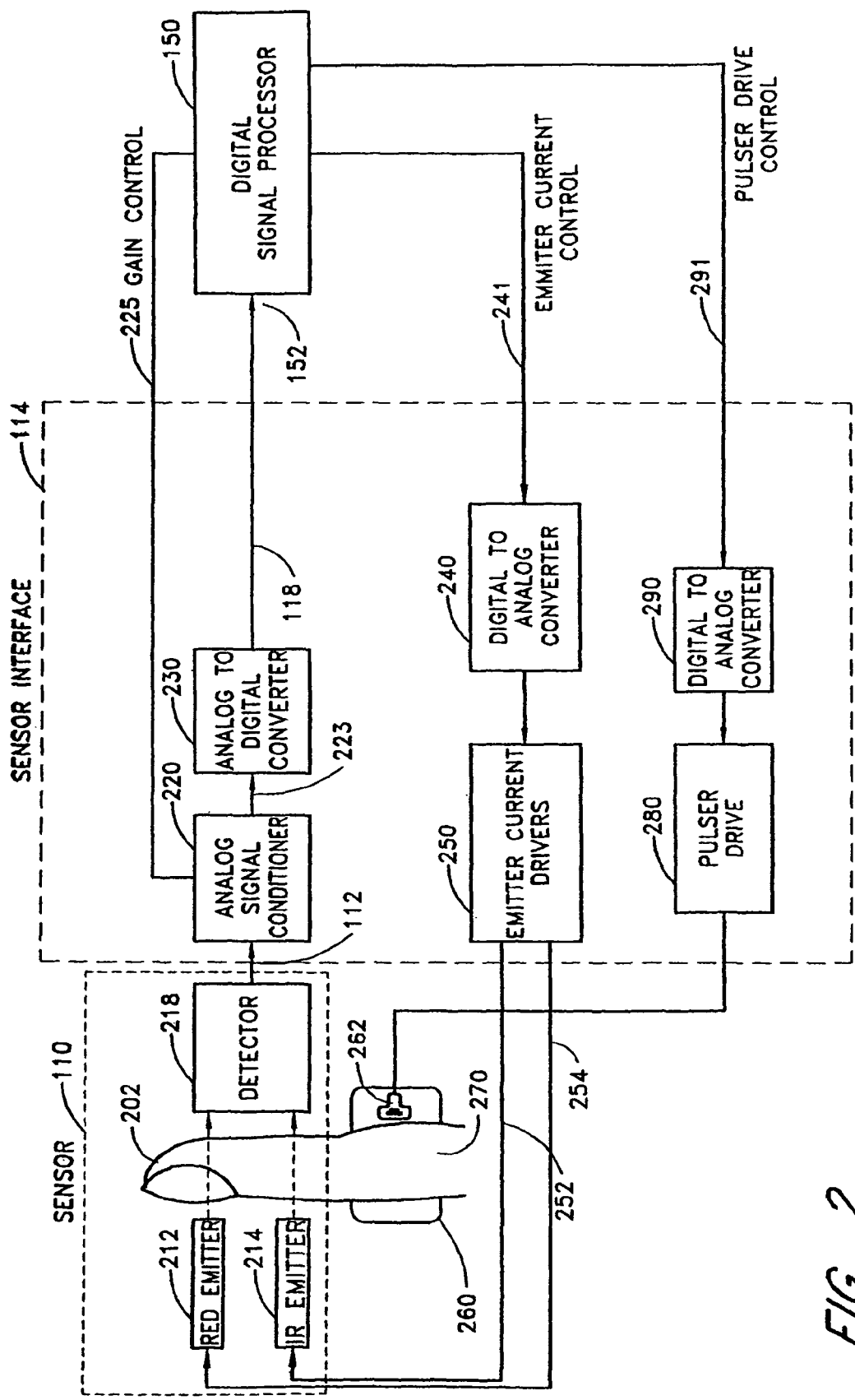
FIG. 2 is a block diagram of the stereo pulse oximeter sensor interface.

FIG. 2 depicts one stereo pulse oximeter data channel having a sensor 110 and a sensor interface 114 providing a single data channel input 152 to the DSP 150. The sensor 110 is used to measure the intensity of red and infrared light after transmission through a portion of the body where blood flows close to the surface, such as a fingertip 202. The sensor 110 has two light emitters, each of which may be, for example, a light-emitting diode (LED). A red emitter 212, which transmits light centered at a red wavelength and an infrared (IR) emitter 214, which transmits light centered at an infrared wavelength are placed adjacent to, and illuminate, a tissue site. A detector 218, which may be a photodiode, is used to detect the intensity of the emitted light after it passes through, and is partially absorbed by, the tissue site. The emitters 212, 214 and detector 218 are secured to the tissue site, with the emitters 212, 214 typically spaced on opposite sides of the tissue site from the detector 218.

To distinguish between tissue absorption at the two wavelengths, the red emitter 212 and infrared emitter 214 are modulated so that only one is emitting light at a given time. In one embodiment, the red emitter 212 is activated for a first quarter cycle and is off for the remaining three-quarters cycle; the infrared emitter 214 is activated for a third quarter cycle and is off for the remaining three-quarters cycle. That is, the emitters 212, 214 are cycled on and off alternately, in sequence, with each only active for a quarter cycle and with a quarter cycle separating the active times. The detector 218 produces an electrical signal corresponding to the red and infrared light energy attenuated from transmission through the patient tissue site 202. Because only a single detector 218 is used, it receives both the red and infrared signals to form a time-division-multiplexed (TDM) signal. This TDM signal is coupled to the input 112 of the sensor interface 114. One of ordinary skill in the art will appreciate alternative activation sequences for the red emitter 212 and infrared emitter 214 within the scope of this invention, each of which provides a time multiplexed signal from the detector 218 allowing separation of red and infrared signals and determination and removal of ambient light levels in downstream signal processing.

To compute $Sp_aO_2$, pulse oximetry relies on the differential light absorption of oxygenated hemoglobin, $HbO_2$, and deoxygenated hemoglobin, Hb, to compute their respective concentrations in the arterial blood. This differential absorption is measured at the red and infrared wavelengths of the sensor 110. The relationship between arterial oxygen saturation and hemoglobin concentration can be expressed as:

$$Sp_aO_2 = 100 \frac{C_{HbO2}}{C_{Hb} + C_{HbO2}} \quad (1)$$

That is, arterial oxygen saturation is the percentage concentration of oxygenated hemoglobin compared to the total concentration of oxygenated hemoglobin and deoxygenated hemoglobin in the arterial blood. $Sp_aO_2$ is actually a measure of the partial oxygen saturation of the hemoglobin because other hemoglobin derivatives, such as COHb and MetHb, are not taken into consideration.

Figure 3:
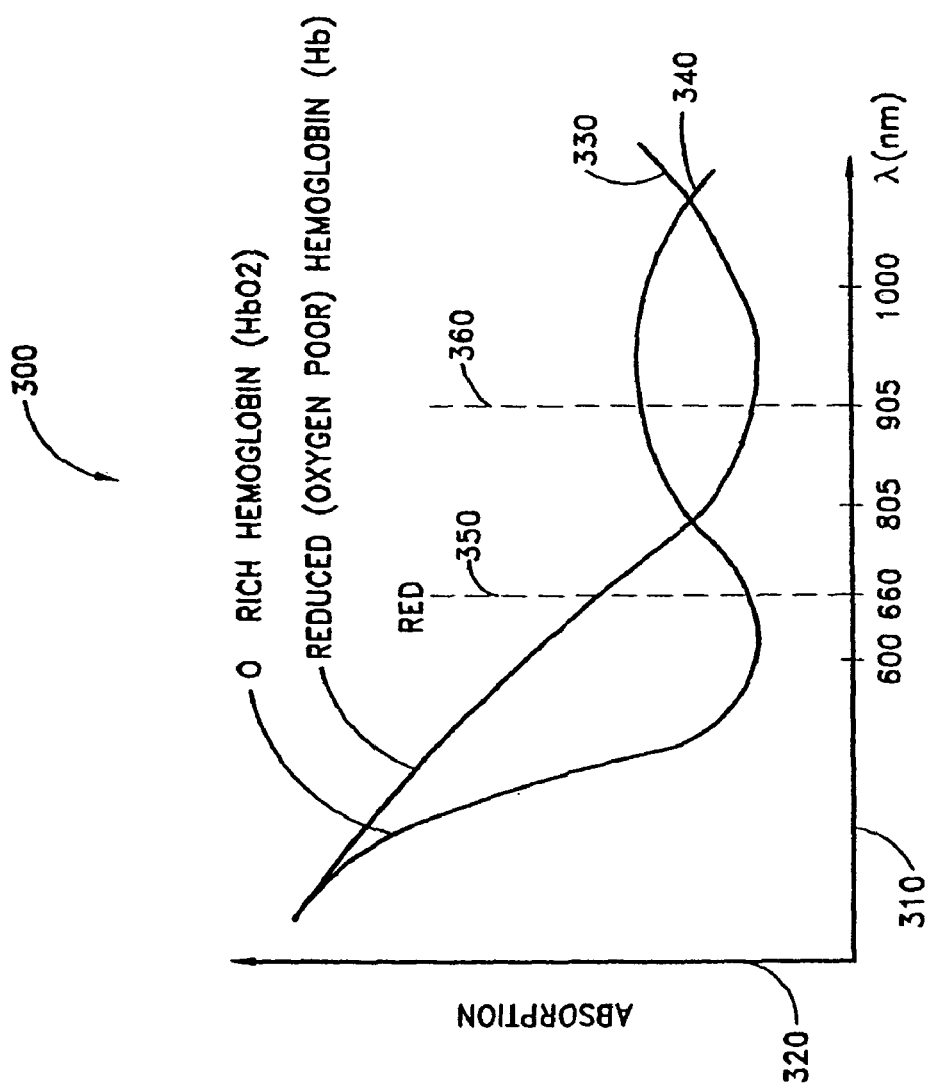
FIG. 3 is a graph illustrating the absorption of red and infrared wavelengths by both oxygenated and deoxygenated hemoglobin.

FIG. 3 shows a graph 300 of the optical absorption properties of $HbO_2$ and $Hb$. The graph 300 has an x-axis 310 corresponding to wavelength and a y-axis 320 corresponding to hemoglobin absorption. An Hb curve 330 shows the light absorption properties of deoxygenated hemoglobin. An $HbO_2$ curve 340 shows the light absorption properties of oxygenated hemoglobin. Pulse oximetry measurements are advantageously made at a red wavelength 350 corresponding to 660 nm and an infrared wavelength 360 corresponding to 905 nm. This graph 300 shows that, at these wavelengths 350, 360, deoxygenated hemoglobin absorbs more red light than oxygenated hemoglobin, and, conversely, oxygenated hemoglobin absorbs more infrared light than deoxygenated hemoglobin.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, etc., each of which absorbs light. It is assumed that the background absorption due to these surrounding tissues is invariant and can be ignored. Thus, blood oxygen saturation measurements are based upon a ratio of the time-varying or AC portion of the detected red and infrared signals with respect to the time-invariant or DC portion. This AC/DC ratio normalizes the signals and accounts for variations in light pathlengths through the measured tissue. Further, a ratio of the normalized absorption at the red wavelength over the normalized absorption at the infrared wavelength is computed:

$$\frac{RD}{IR} = \frac{\left(\frac{Red_{AC}}{Red_{DC}}\right)}{\left(\frac{IR_{AC}}{IR_{DC}}\right)} \quad (2)$$

where $Red_{AC}$ and $IR_{AC}$ are the root-mean-square (RMS) of the corresponding time-varying signals. This "red-over-infrared, ratio-of-ratios" cancels the pulsatile signal. The desired $Sp_aO_2$ measurement is then computed from this ratio.

Figure 4:
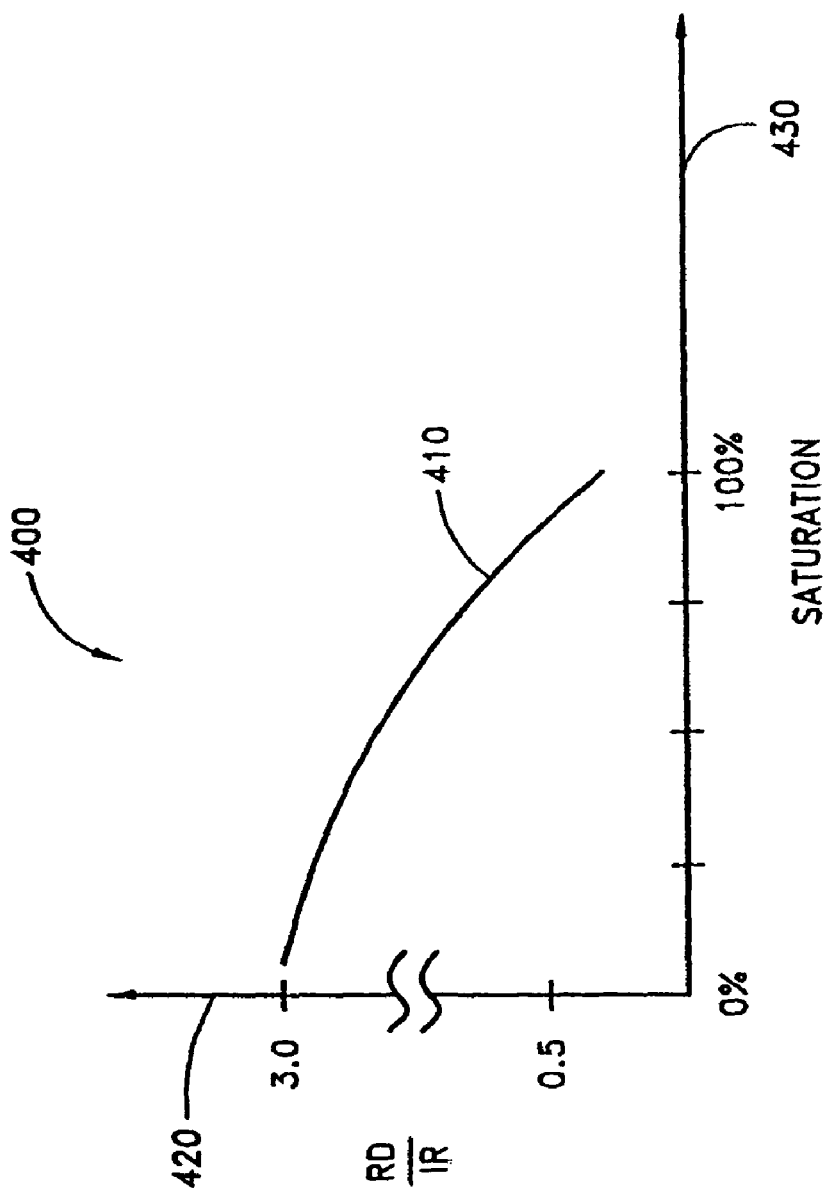
FIG. 4 is a graph showing the empirical relationship between the "red over infrared" ratio and arterial oxygen saturation.

FIG. 4 shows a graph 400 depicting the relationship between RD/IR and $Sp_aO_2$. This relationship can be approximated from Beer-Lambert's Law, as outlined below. However, it is most accurately determined by statistical regression of experimental measurements obtained from human volunteers and calibrated measurements of oxygen saturation. The result can be depicted as a curve 410, with measured values of RD/IR shown on a y-axis 420 and corresponding saturation values shown on an x-axis 430. In a pulse oximeter device, this empirical relationship can be stored in a read-only memory (ROM) look-up table so that $Sp_aO_2$ can be directly read-out from input RD/IR measurements.

According to the Beer-Lambert law of absorption, the intensity of light transmitted through an absorbing medium is given by:

$$I = I_0 \exp\left(-\sum_{i=1}^{N} \varepsilon_{i\lambda} c_i x_i\right) \quad (3)$$

where $I_0$ is the intensity of the incident light, $\varepsilon_{i,\lambda}$ is the absorption coefficient of the $i^{th}$ constituent at a particular wavelength $\lambda$, $c_i$ is the concentration coefficient of the $i^{th}$ constituent and $x_i$ is the optical path length of the $i^{th}$ constituent. As stated above, assuming the absorption contribution by all constituents but the arterial blood is constant, taking the natural logarithm of both sides of equation (3) and removing time invariant terms yields:

$$\ln(I) = -[\varepsilon_{HbO2,\lambda} C_{HbO2} + \varepsilon_{Hb,\lambda} C_{Hb}] X(t) \quad (4)$$

Measurements taken at both red and infrared wavelengths yield:

$$RD(t) = -[\varepsilon_{HbO2,RD} C_{HbO2} + \varepsilon_{Hb,RD} C_{Hb}] X_{RD}(t) \quad (5)$$

$$IR(t) = -[\varepsilon_{HbO2,IR} C_{HbO2} + \varepsilon_{Hb,IR} C_{Hb}] X_{IR}(t) \quad (6)$$

Taking the ratio RD(t)/IR(t) and assuming $X_{RD}(t) \approx X_{IR}(t)$ yields:

$$RD/IR = [\varepsilon_{HbO2,RD} C_{HbO2} + \varepsilon_{Hb,RD} C_{Hb}] / [\varepsilon_{HbO2,IR} C_{HbO2} + \varepsilon_{Hb,IR} C_{Hb}] \quad (7)$$

Assuming further that:

$$C_{HbO2} + C_{Hb} = 1 \quad (8)$$

then equation (1) can be solved in terms of RD/IR yielding a curve similar to the graph 400 of FIG. 4.

Sensor Interface

FIG. 2 also depicts the sensor interface 114 for one data channel. An interface input 112 from the sensor 110 is coupled to an analog signal conditioner 220. The analog signal conditioner 220 has an output 223 coupled to an analog-to-digital converter (ADC) 230. The ADC output 118 is coupled to the DSP 150. The analog signal conditioner also has a gain control input 225 from the DSP 150. The functions of the analog signal conditioner 220 are explained in detail below. The ADC 230 functions to digitize the input signal 112 prior to further processing by the DSP 150, as described below. The sensor interface 114 also has an emitter current control input 241 coupled to a digital-to-analog converter (DAC) 240. The DSP provides control information to the DAC 240 via the control input 241 for a pair of emitter current drivers 250. One driver output 252 couples to the red emitter 212 of the sensor 110, and another driver output 254 couples to the IR emitter 214 of the sensor 110.

Figure 5:
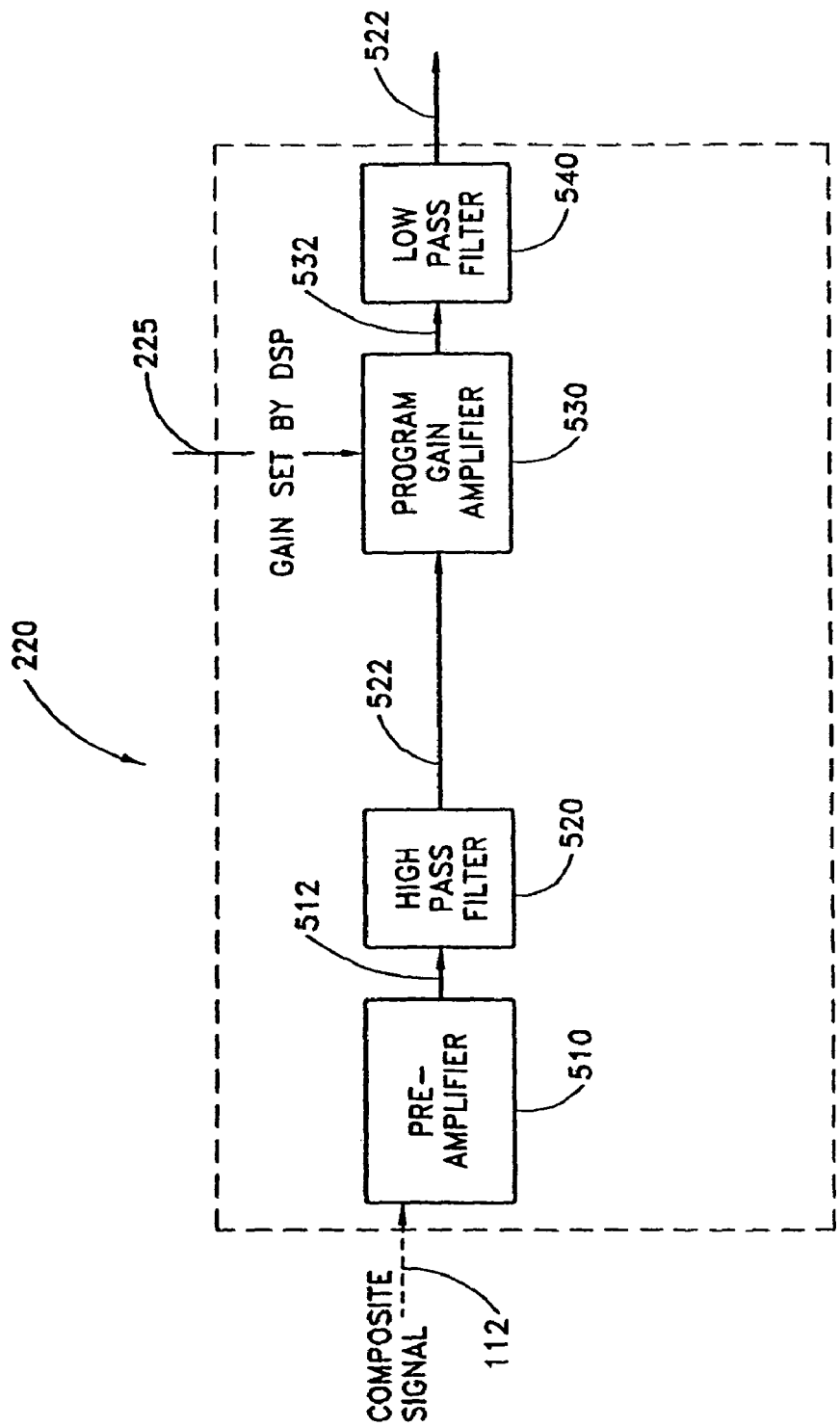
FIG. 5 is a block diagram of the analog signal conditioning for the sensor interface.

FIG. 5 illustrates one embodiment of the analog signal conditioner 220. The analog signal conditioner 220 receives a composite intensity signal 112 from the sensor detector 218 (FIG. 2) and then filters and conditions this signal prior to digitization. The embodiment shown has a preamplifier 510, a high pass filter 520, a programmable gain amplifier 530 and a low pass filter 540. The low pass filter output 223 is coupled to the ADC 230 (FIG. 2). The preamplifier 510 converts the current signal 112 from the detector 218 (FIG. 2) to a corresponding amplified voltage signal. The gain in the preamplifier 510 is selected in order to prevent ambient light in the signal 112 from saturating the preamplifier 510 under normal operating conditions. The preamplifier output 512 is coupled to the high pass filter 520, which removes the DC component of the detector signal 112. The corner frequency of the high pass filter 520 is set well below the multiplexing frequency of the red and infrared emitters 212, 214 (FIG. 2). The high pass filter output 522 couples to the programmable gain amplifier 530, which also accepts a programming input 225 from the DSP 150 (FIG. 2). This gain is set at initialization or at sensor placement to compensate for variations from patient to patient. The programmable gain amplifier output 532 couples to a low-pass filter 540 to provide anti-aliasing prior to digitization.

As described above, pulse oximetry measurements rely on the existence of a pulsatile signal. The natural heart beat provides a pulsatile signal that allows measurement of arterial oxygen saturation. In the systemic circulation, all arterial pulsations are damped before flow enters the capillaries, and none are transmitted into the veins. Thus, there is no arterial pulse component in the venous blood and absorption caused by venous blood is assumed canceled by the ratio-of-ratio operation described above. Venous blood, being at a relatively low pressure, will "slosh back and forth" during routine patient motions, such as shivering, waving and tapping. This venous blood sloshing creates a time-varying signal that is considered "noise" and can easily overwhelm conventional ratio-based pulse oximeters. Advanced pulse oximetry techniques allow measurement of $Sp_vO_2$ under these circumstances. For example, such advanced techniques are disclosed in U.S. Pat. No. 5,632,272, which is assigned to the assignee of the current application. This measurement is only available during motion or other physiological events causing a time-varying venous signal.

The venous blood may also have a pulsatile component at the respiration rate, which can be naturally induced or ventilator induced. In adults, the natural respiration rate is 10-15 beats per minute (bpm). In neonates, this natural respiration rate is 30-60 bpm. The ventilator induced pulse rate depends on the ventilator frequency. If this respiration induced venous pulse is of sufficient magnitude, advanced pulse oximetry techniques, described below, allow measurement of $Sp_vO_2$.

A controlled physiological event, however, can be created that allows for a continuous measurement of venous oxygen saturation, independent of motion or respiration. U.S. Pat. No. 5,638,816, which is assigned to the assignee of the current application discloses a technique for inducing an intentional active perturbation of the blood volume of a patient, and is referred to as an "active pulse." Because peripheral venous oxygen saturation, $Sp_vO_2$, is a desirable parameter for stereo pulse oximetry applications, it is advantageous to provide for a continuous and controlled pulsatile venous signal.

FIG. 2 depicts an active pulse mechanism used in conjunction with a pulse oximetry sensor. An active pulser 260 physically squeezes or otherwise perturbs a portion of patient tissue 270 in order to periodically induce a "pulse" in the blood at the tissue site 202. A pulser drive 280 generates a periodic electrical signal to a transducer 262 attached to the patient. The transducer 262 creates a mechanical force against the patient tissue 270. For example, the pulser 260 could be a solenoid type device with a plunger that presses against the fleshy tissue to which it is attached. The DSP 150 provides pulse drive control information to a digital to analog converter (DAC) 290 via the control input 291. The DAC output 292 is coupled to the pulser drive 280. This allows the processor to advantageously control the magnitude of the induced pulse, which moderates scattering as described below. The pulser 260 could be a pressure device as described above. Other pressure mechanisms, for example a pressure cuff, could be similarly utilized. Other methods, such as temperature fluctuations or other physiological changes, which physiologically alter a fleshy medium of the body on a periodic basis to modulate blood volume at a nearby tissue site could also be used. Regardless of the active pulse mechanism, this modulated blood volume is radiated by a pulse oximeter sensor and the resulting signal is processed by the signal processing apparatus described below to yield $Sp_vO_2$.

Signal Processor

Figure 6:
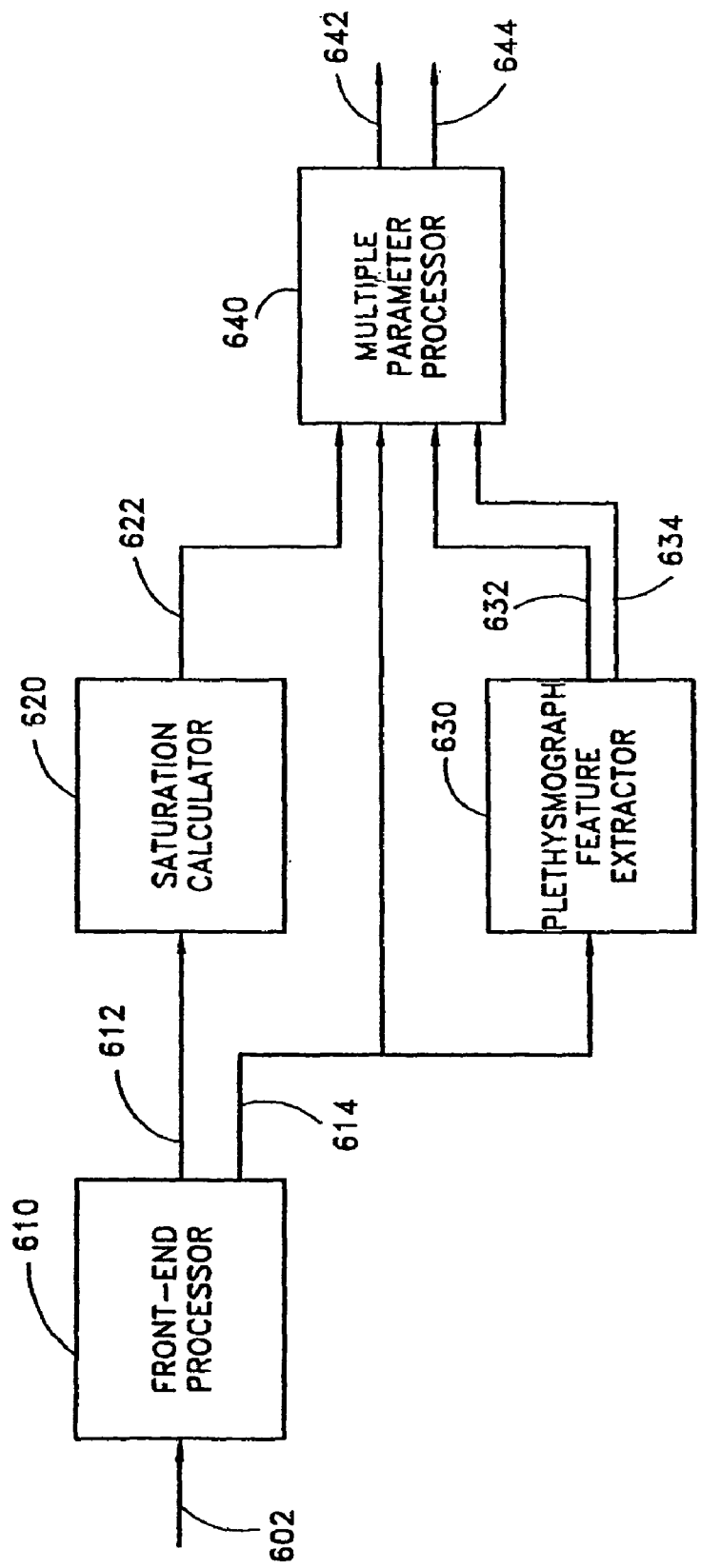
FIG. 6 is a functional block diagram of the stereo pulse oximeter signal processing.

FIG. 6 illustrates the processing functions of the digital signal processor (DSP) 150 (FIG. 1A). Each data channel input 152, 154, 158 (FIG. 1A) is operated on by one or more of the front-end processor 610, saturation calculator 620, plethysmograph feature extractor 630 and multiple parameter processor 640 functions of the DSP 150. First, a digitized signal output from the ADC 230 (FIG. 2) is input 602 to the front-end processor 610, which demultiplexes, filters, normalizes and frequency transforms the signal, as described further below. A front-end output 612 provides a red signal spectrum and an IR signal spectrum for each data channel as inputs to the saturation calculator 620. Another front-end output 614 provides a demultiplexed, normalized IR plethysmograph for each data channel as an input to the feature extractor 630. The saturation calculator output 622 provides arterial and venous saturation data for each data channel as input to the multiple parameter processor 640. One feature extractor output 632 provides data on various plethysmograph shape parameters for each data channel as input into the multiple parameter processor 640. Another feature extractor output 634, also coupled to multiple parameter processor 640, provides an indication of plethysmograph quality and acts as a threshold for determining whether to ignore portions of the input signal 602. The multiple parameter processor has a numerical output 642 that provides same-channel $\Delta$sat parameters and cross-channel parameters, such as $\Delta sat_{xy}$ or $\Delta pleth_{xy}$ to a display 180 (FIG. 1A). The numeric output 642 may also provide saturation and plethysmograph parameters directly from the saturation calculator 620 or the feature extractor 630 without further processing other than data buffering. The multiple parameter processor also has a graphical output 644 that provides plethysmograph waveforms for each data channel in addition to graphics, depending on a particular application, the indicate the trend of the numerical parameters described above.

Front-End Processor

Figure 7:
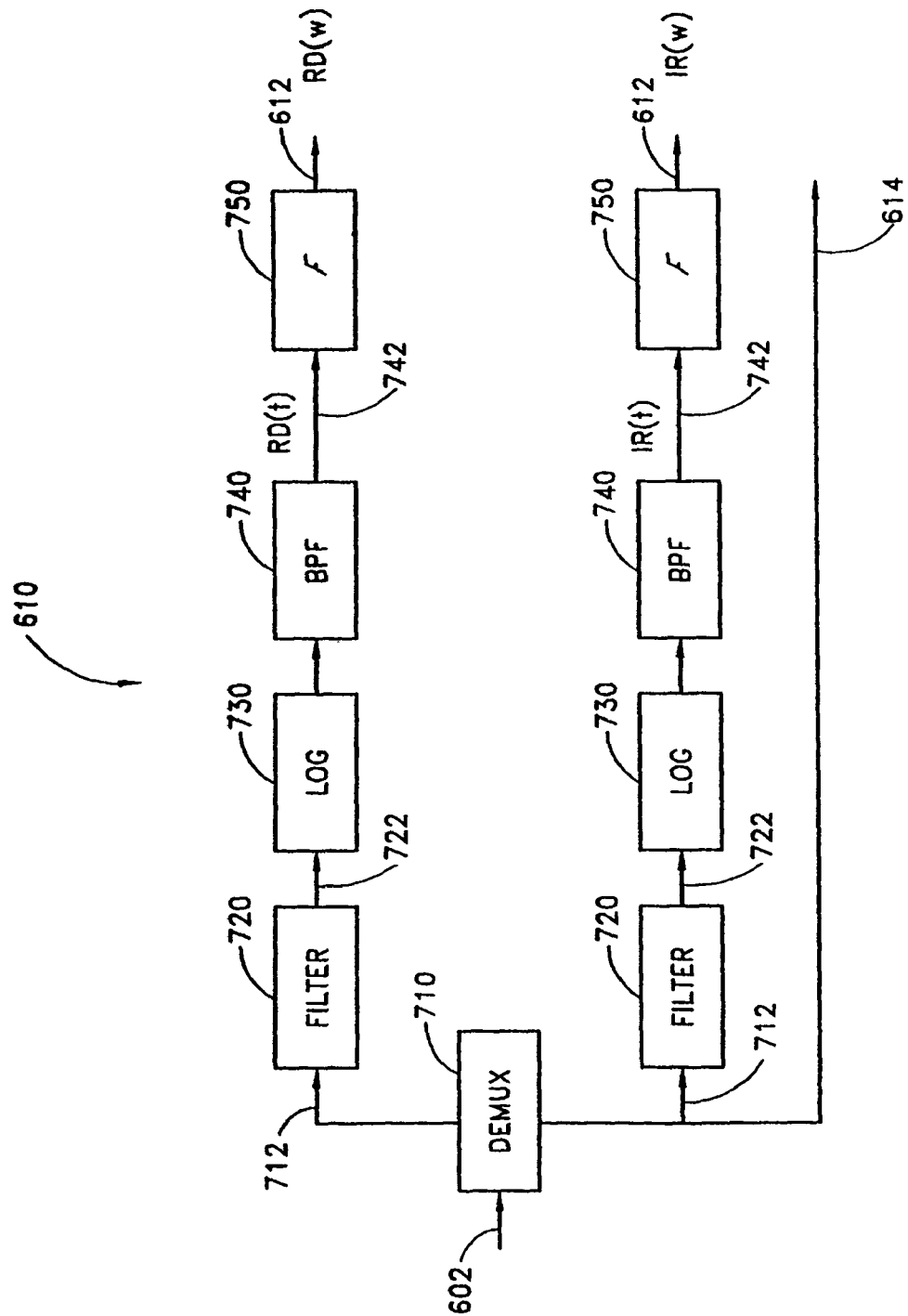
FIG. 7 is a functional block diagram of the front-end signal processing.

FIG. 7 is a functional block diagram of the front-end processor 610 for the stereo pulse oximeter. The digitized sensor output 118 (FIG. 2) is an input signal 602 to a demultiplexer 710, which separates the input signal 602 into a red signal 712 and an infrared signal 714. The separated red and infrared signals 712, 714 are each input to a filter 720 to remove unwanted artifacts introduced by the demultiplexing operation. In one embodiment, the filter 720 is a finite-impulse-response, low-pass filter that also "decimates" or reduces the sample rate of the red and infrared signals 712, 714. The filtered signals 722 are then each normalized by a series combination of a log function 730 and bandpass filter 740. The normalized signals, RD(t), IR(t) 742 are coupled to a Fourier transform 750, which provides red frequency spectrum and infrared frequency spectrum outputs, RD($\omega$), IR($\omega$) 612. A demultiplexed infrared signal output 614 is also provided.

Saturation Calculator

Figure 8:
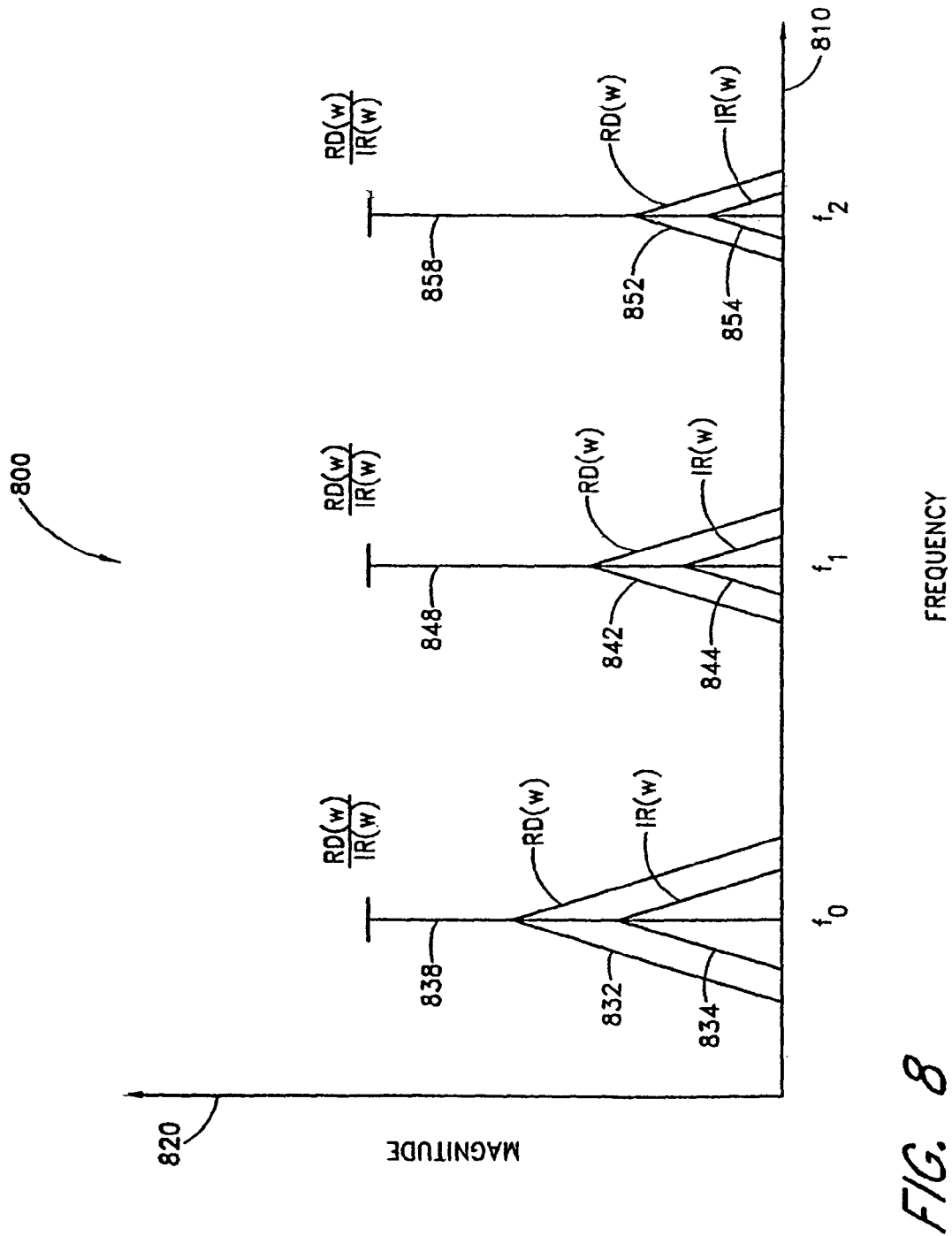
FIG. 8 is a graph depicting the frequency spectrum of an arterial intensity signal.

FIG. 8 shows a graph 800 illustrating idealized spectrums of RD(t) and IR(t) 752 (FIG. 7). The graph has an x-axis 810 that corresponds to the frequency of spectral components in these signals and a y-axis 820 that corresponds to the magnitude of the spectral components. The spectral components are the frequency content of RD(t) and IR(t), which are plethysmograph signals corresponding to the patient's pulsatile blood flow, as described below. Thus, the frequencies shown along the x-axis 810, i.e. $f_0$, $f_1$, $f_2$, are the fundamental and harmonics of the patient's pulse rate. The spectrum of RD(t), denoted RD($\omega$) 612 (FIG. 7), is shown as a series of peaks, comprising a first peak 832 at a fundamental frequency, $f_0$, a second peak 842 at a first harmonic, $f_1$ and a third peak 852 at a second harmonic, $f_2$. Similarly, the spectrum of IR(t), denoted IR($\omega$) 612 (FIG. 7), is shown as another series of peaks, comprising a first peak 834 at a fundamental frequency, $f_0$, a second peak 844 at a first harmonic, $f_1$ and a third peak 854 at a second harmonic, $f_2$. Also shown in FIG. 8 is the ratio of the spectral peaks of RD(t) and IR(t), denoted RD($\omega$)/IR($\omega$). This ratio is shown as a first ratio line 838 at the fundamental frequency $f_0$, a second ratio line 848 at the first harmonic $f_1$, and a third ratio line 858 at the second harmonic $f_2$.

The magnitude of these ratio lines RD($\omega$)/IR($\omega$) corresponds to the ratio RD/IR defined by equation (2), and, hence, can be used to determine $Sp_aO_2$. This can be seen from Parseval's relation for a periodic signal, x(t), having a period T, where $X_k$ is the spectral component at the kth harmonic of x(t):

$$\frac{1}{T}\int_0^T (|x(t)|)^2 \, dt = \sum_k (|X_k|)^2 \qquad (9)$$

Equation (9) relates the energy in one period of the signal x(t) to the sum of the squared magnitudes of the spectral components. The term $|X_k|^2$ can be interpreted as that part of the energy per period contributed by the kth harmonic. In an ideal measurement, the red and infrared signals are the same to within a constant scale factor, which corresponds to the arterial oxygen saturation. Likewise, the red and infrared spectra are also the same to within a constant scale factor. Thus, in an ideal measurement, all of the ratio lines 838, 848, 858 have substantially the same amplitude. Any differences in the amplitude of the ratio lines is likely due to motion, scattering or other noise contaminations, as discussed further below. Accordingly, any of the RD($\omega$)/IR($\omega$) ratio lines is equivalent to the ratio, RD/IR, of equation (2) and can be used to derive $Sp_aO_2$.

One skilled in the art will recognize that the representations in FIG. 8 are idealized. In particular, in actual measured data, especially if contaminated by noise, the frequencies of the peaks of RD($\omega$) do not correspond exactly to the frequencies of the peaks of IR($\omega$). For example, the fundamental frequency, $f_0$, found for RD($\omega$) will often be different from the fundamental frequency, $f_0'$, found for IR($\omega$) and similarly for the harmonics of $f_0$.

Figure 9:
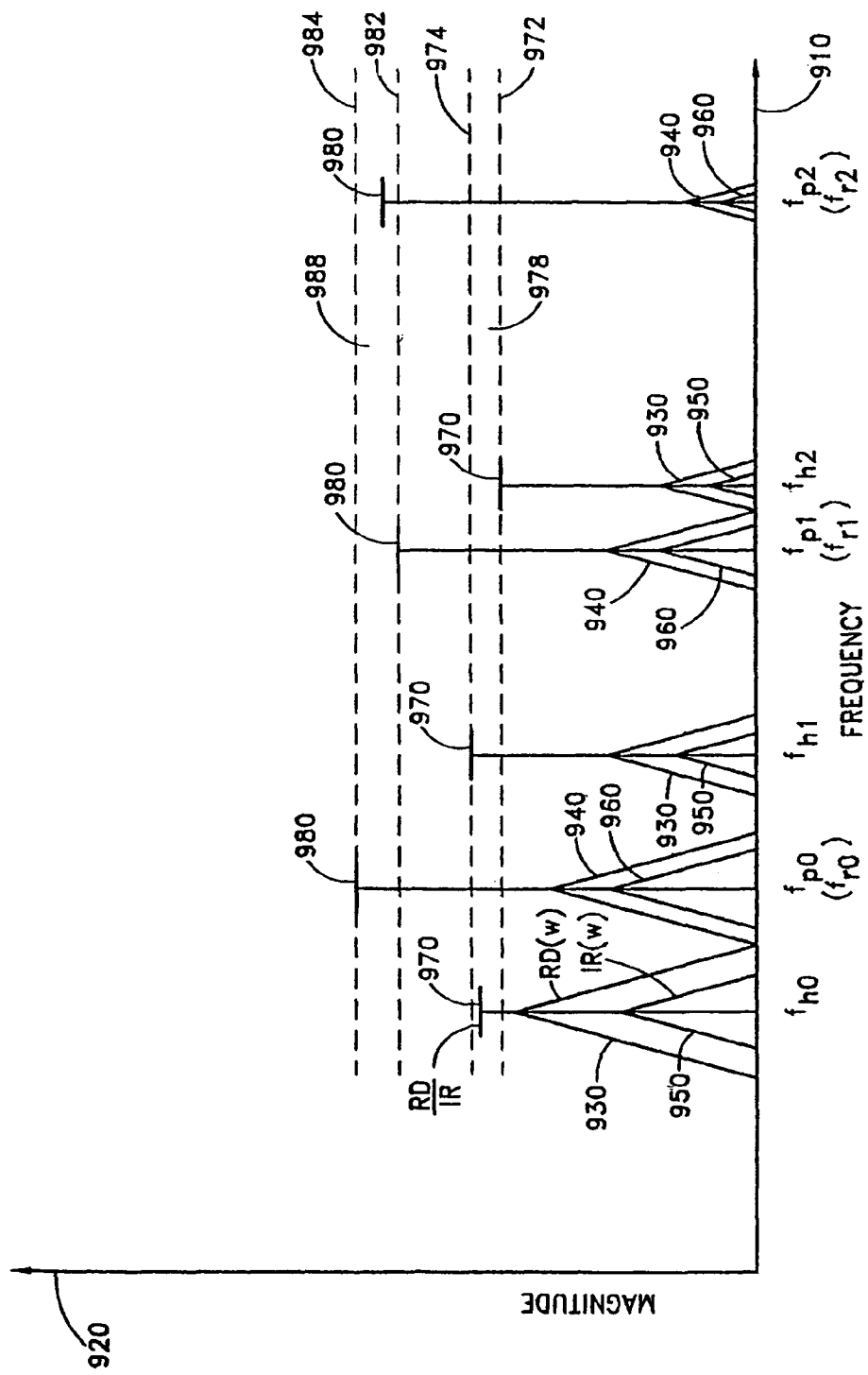
FIG. 9 is a graph depicting the frequency spectrum of a combined arterial and venous intensity signal.

FIG. 9 shows a graph 900 illustrating idealized spectrums RD($\omega$) and IR($\omega$) and associated ratio lines measured with an active pulse sensor. The graph 900 has an x-axis 910 that corresponds to the frequency of spectral components in these signals and a y-axis 920 that corresponds to the magnitude of the spectral components. The spectrum, RD($\omega$), is shown as two series of peaks. One series of peaks 930 occurs at a fundamental frequency, $f_{h0}$, and associated harmonics, $f_{h1}$ and $f_{h2}$, of the patient's pulse (heart) rate. Another series of peaks 940 occurs at a fundamental frequency, $f_{p0}$, and associated harmonics, $f_{p1}$ and $f_{p2}$, of the active pulse rate. Similarly, the spectrum, IR($\omega$), is shown as two series of peaks. One series of peaks 950 occurs at a fundamental frequency, $f_{h0}$, and associated harmonics, $f_{h1}$ and $f_{h2}$, of the patient's pulse rate. Another series of peaks 960 occurs at a fundamental frequency, $f_{p0}$, and associated harmonics, $f_{p1}$ and $f_{p2}$, of the active pulse rate. Accordingly, there are two series of RD/IR ratio lines. One series of ratio lines 970 are at the patient's pulse rate and associated harmonics, and another series of ratio lines 980 are at the active pulser rate and associated harmonics.

Because only the arterial blood is pulsatile at the patient's pulse rate, the ratio lines 970 are only a function of the arterial oxygen saturation. Accordingly, $Sp_aO_2$ can be derived from the magnitude of these ratio lines 970, as described above. Further, a modulation level for the active pulse is selected which insignificantly perturbates the arterial blood while providing a measurable venous signal. This is possible because the arterial blood pressure is significantly larger than the venous pressure. The modulation level is regulated as described above with respect to FIG. 2, i.e. the DSP 150, via a pulser drive control 291, sets the magnitude of the pulser drive 280 to the pulse inducing mechanism 262. Assuming that the active pulse modulation of the arterial blood is insignificant, only the venous blood is pulsatile at the active pulser rate. Hence, the ratio lines 980 are only a function of the venous oxygen saturation. Accordingly, $Sp_aO_2$ can be derived from the magnitude of the pulse rate related ratio lines 980 in the same manner as $Sp_aO_2$ is derived from the magnitude of the pulse rate related ratio lines.

Scattering

Propagation of optical radiation through tissue is affected by absorption and scattering processes. The operation of pulse oximeters was described qualitatively above using an analysis based on the Beer-Lambert law of absorption, equation (3). This approach, however, fails to account for the secondary effects of light scattering at pulse oximeter wavelengths. The primary light scatterer in blood is erythrocytes, i.e. red blood cells. A qualitative understanding of the effects of scattering on pulse oximetry is aided by a description of red blood cell properties within flowing blood.

Human blood is a suspension of cells in an aqueous solution. The cellular contents are essentially all red blood cells, with white cells making up less the $\frac{1}{600}^{th}$ of the total cellular volume and platelets less than $\frac{1}{800}^{th}$ of the total cellular volume. Normally the hematocrit, which is the percentage of the total volume of blood occupied by cells, is about 50% in large vessels and 25% in small arterioles or venules.

Red blood cells are extremely deformable, taking on various shapes in response to the hydrodynamic stresses created by flowing blood. For example, assuming a laminar blood flow within a vessel, a parabolic velocity profile exists that is greatest in the vessel center and smallest along the vessel walls. Nominally, red blood cells are shaped as biconcave disks with a diameter of 7.6 um and thickness of 2.8 um. Exposed to this velocity profile, the red blood cells become parachute-shaped and aligned in the direction of the blood flow. Thus, during systole, transmitted light is scattered by aligned, parachute-shaped cells. During diastole, the light is scattered by biconcave disks having a more or less random alignment.

The time-varying shape and alignment of the red blood cells can have a significant effect on measured values of oxygen saturation if scattering is ignored. Analogous to the analysis using the Beer-Lambert absorption law, scattering can be qualitatively understood as a function of the scattering coefficients of various tissues. Specifically, the bulk scattering coefficient can be written as:

$$\mu_s = V_b \mu_b + V_t \mu_t \qquad (10)$$

where $V_b$ is the blood volume, $\mu_b$ is the scattering coefficient of blood, $V_t$ is the surrounding tissue volume and $\mu_t$ is the scattering coefficient of the surrounding tissue. The volume, $V_t$, and scattering coefficient, $\mu_t$, of the surrounding tissue are time invariant. The blood volume, $V_b$, however, is pulsatile. The ratio of ratios computation, RD/IR, results in normalization of the time invariant or DC tissue absorption and cancellation of the time varying or AC pulsatile blood volume absorption to yield a number related to oxygen saturation. This computational approach is valid because the absorption coefficients of blood, $\epsilon_{HbO2,\lambda}$, $\epsilon_{Hb,\epsilon}$ given in equation (4) were assumed to change only slowly over time. The scattering coefficient of blood $.\mu_b$, however, is time variant. As described above, this variation is due to the time-varying alignment and shape of the red blood cells. This time variation in the detected intensity of light transmitted through a tissue site is not normalized or canceled by the RD/IR calculation. Further, because the magnitude of the scattering coefficient variations is a function of blood flow, these variations become more pronounced with larger pulses in the blood supply. As a result, scattering produces frequency-dependent magnitude variations in the ratio lines RD($\omega$)/IR($\omega$).

FIG. 9 illustrates the effect of scattering on the spectra of the detected red and infrared intensity waveforms. When these waveforms are transformed into the frequency domain, the time varying component of scattering manifests itself as spreads 978, 988 in the RD/IR ratio lines at each harmonic of the plethysmograph or active pulse rate. The magnitude of the ratio lines 970 at the fundamental and harmonics of the patient's pulse rate varies between a minimum 972 and a maximum 974, resulting in a magnitude spread 978. Similarly, the magnitude of the ratio lines 980 at the fundamental and harmonics of the active pulse rate varies between a minimum 982 and a maximum 984, resulting in a magnitude spread 988. Normally, absent motion artifact or noise contamination, the spread 978, 988 in the ratio lines is quiet small, but the magnitude of these spreads 978, 988, increases with larger blood flows or pulse magnitudes. Scattering attributable to an active pulse can be regulated by adjusting the magnitude of the active pulse modulation based upon the amount of spread 978, 988 of the ratio line magnitudes. Thus, the active pulse magnitude can be increased to obtain a larger detected AC signal, but limited to below the point at which scattering becomes significant.

Figure 10:
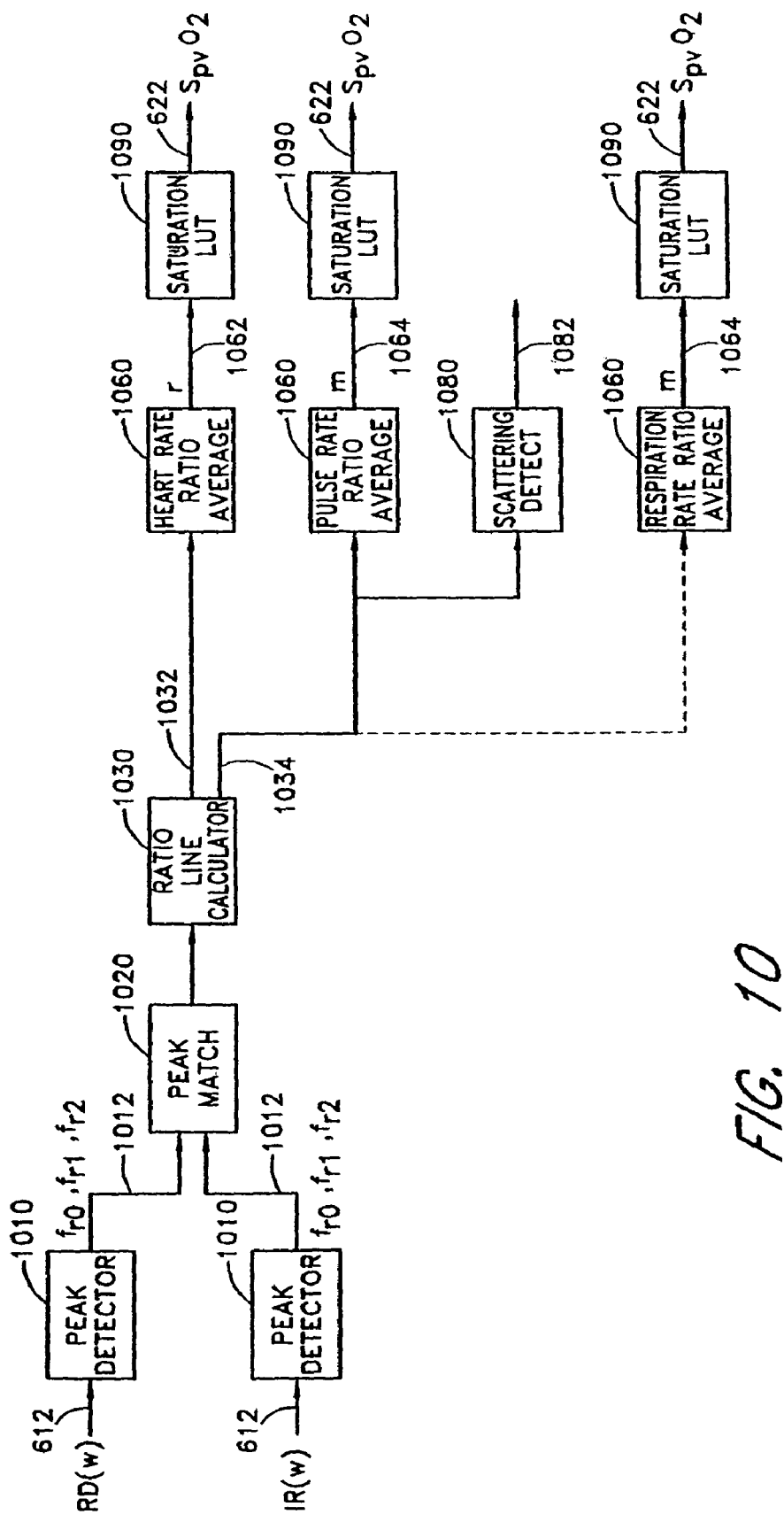
FIG. 10 is a functional block diagram of the saturation calculation signal processing.

FIG. 10 depicts an embodiment of the signal processing for determining oxygen saturation from the ratio lines of RD($\omega$)/RD($\omega$). The red spectrum RD($\omega$) 612 and infrared spectrum IR($\omega$) 612, computed as described above with respect to FIG. 7, are input to a peak detector 1010. The peak detector 1010 separately calculates localized maximums for RD($\omega$) and IR($\omega$). The peak detector output 1012 is a series of frequencies corresponding to the patient pulse rate fundamental and harmonics. If an active pulse is used, the peak detector output 1012 is also a series of frequencies corresponding to the active pulse rate. Although the active pulse rate is known, the detected peaks may have been shifted due to noise, motion artifact or other signal contamination. The peak detector output 1012 is coupled to a series combination of peak matcher 1020 and ratio line calculator 1030. The ratio lines RD/IR are calculated by matching the frequency peaks of RD($\omega$) with the nearest frequency peaks of IR($\omega$). The ratio lines associated with the pulse rate harmonics 1032 are then separated into a different set from the ratio lines associated with the active pulse harmonics 1034, assuming an active pulse is utilized. An average ratio line for each set 1032, 1034 is calculated by averaging 1060 all ratio lines in a set. The magnitude of the average ratio line r 1062 for the pulse rate set 1032 is then fed to a look-up table (LUT) 1090, which provides an output 622 of the measured value of $Sp_aO_2$. Similarly, if an active pulse is used, the magnitude of the average ratio line $\mu$ 1064 for the active pulse rate set 1034 is then fed to a LUT 1090, which provides an output 622 of the measured value of $Sp_vO_2$. A scattering detector 1080 computes the spread 988 (FIG. 9) in the set of ratio lines associated with the active pulse and provides this value 1082 to the DSP 150 (FIG. 2) so that the DSP can set the pulser drive control 291 (FIG. 2) to regulate the magnitude of the active pulse.

Alternatively, $Sp_vO_2$ may be measured from respiration-induced pulses in the venous blood, described above, without utilizing an active pulse sensor. Specifically, a series of ratio lines 980 (FIG. 9) would occur at a fundamental frequency, $f_{r0}$, and associated harmonics, $f_{r1}$ and $f_{r2}$, of the respiration rate, which is either known from the ventilator frequency or derived from a separate measurement of the natural respiration. As shown in FIG. 10, the ratio lines associated with the respiration rate harmonics 1034 are then separated into a different set from the ratio lines associated with the pulse rate harmonics 1032. An average ratio line for the respiration rate set 1034 is calculated by averaging 1060 all ratio lines in that set. The magnitude of the average ratio line $\mu$ 1064 for the respiration rate set 1034 is then fed to a look-up table (LUT) 1090, which provides an output 622 of the measured value of $Sp_vO_2$.

Plethysmograph Feature Extractor

Figure 11:
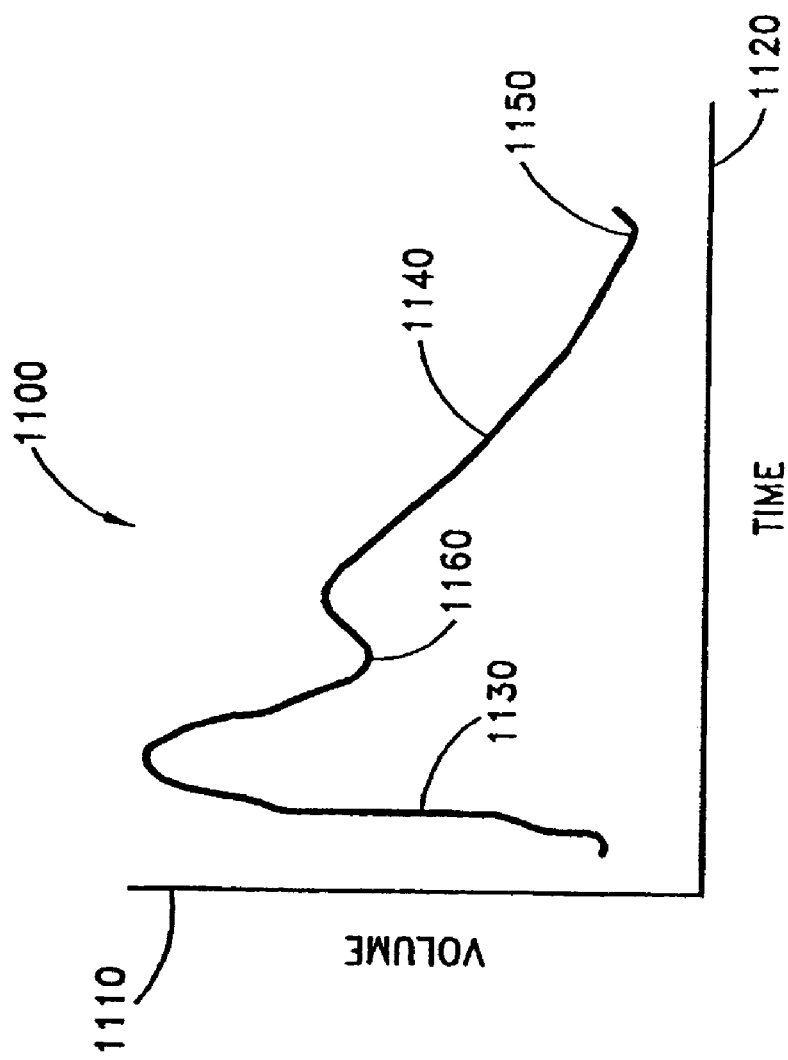
FIG. 11 is a graph illustrating a plethysmograph waveform.

FIG. 11 illustrates the standard plethysmograph waveform 1100, which can be derived from a pulse oximeter. The waveform 1100 is a visualization of blood volume change in the illuminated peripheral tissue caused by arterial blood flow, shown along the y-axis 1110, over time, shown along the x-axis 1120. The shape of the plethysmograph waveform 1100 is a function of heart stroke volume, pressure gradient, arterial elasticity and peripheral resistance. The ideal waveform 1100 displays a broad peripheral flow curve, with a short, steep inflow phase 1130 followed by a 3 to 4 times longer outflow phase 1140. The inflow phase 1130 is the result of tissue distention by the rapid blood volume inflow during ventricular systole. During the outflow phase 1140, blood flow continues into the vascular bed during diastole. The end diastolic baseline 1150 indicates the minimum basal tissue perfusion. During the outflow phase 1140 is a dicrotic notch 1160, the nature of which is disputed. Classically, the dicrotic notch 1160 is attributed to closure of the aortic valve at the end of ventricular systole. However, it may also be the result of reflection from the periphery of an initial, fast propagating, pressure pulse that occurs upon the opening of the aortic valve and that precedes the arterial flow wave. A double dicrotic notch can sometimes be observed, although its explanation is obscure, possibly the result of reflections reaching the sensor at different times.

Figure 12:
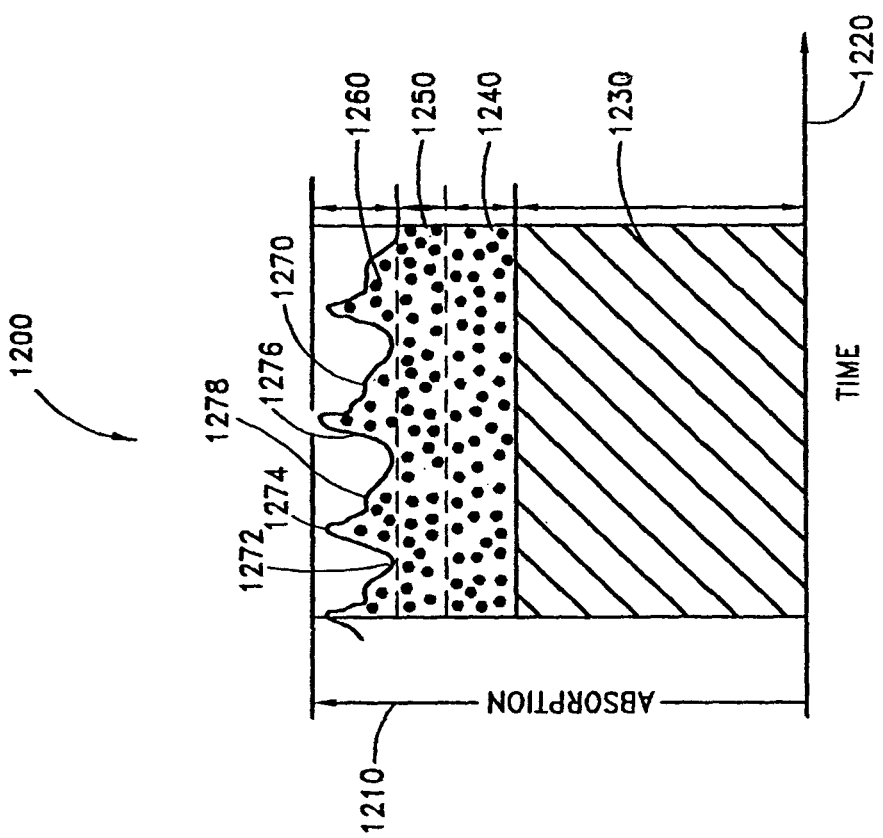
FIG. 12 is a graph illustrating the absorption contribution of various blood and tissue components.

FIG. 12 is a graph 1200 illustrating the absorption of light at a tissue site illuminated by a pulse oximetry sensor. The graph 1200 has a y-axis 1210 representing the total amount of light absorbed the tissue site, with time shown along an x-axis 1220. The total absorption is represented by layers including the static absorption layers due to tissue 1230, venous blood 1240 and a baseline of arterial blood 1250. Also shown is a variable absorption layer due to the pulse-added volume of arterial blood 1260. The profile 1270 of the pulse-added arterial blood 1260 is seen as the plethysmograph waveform 1100 depicted in FIG. 11.

Figure 13:
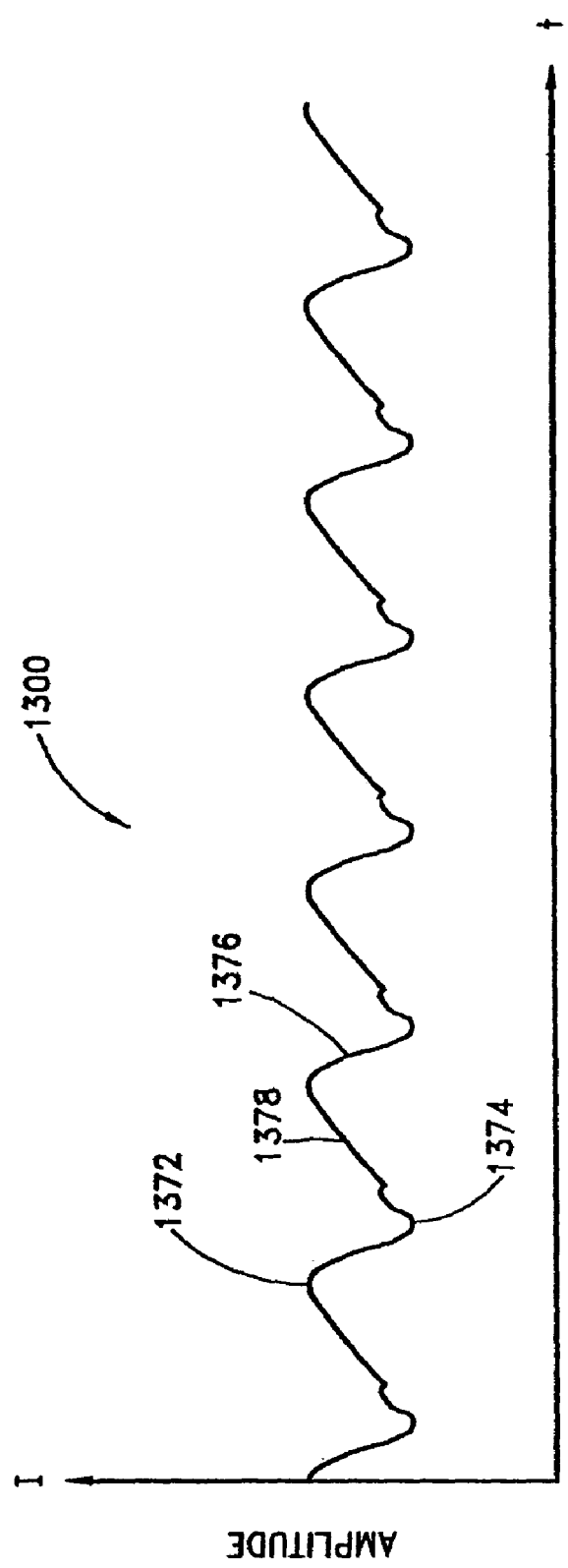
FIG. 13 is a graph illustrating an intensity "plethysmograph" pulse oximetry waveform.

FIG. 13 illustrates the photoplethysmograph intensity signal 1300 detected by a pulse oximeter sensor. A pulse oximeter does not directly detect absorption, and hence does not directly measure the standard plethysmograph waveform 1100 (FIG. 11). However, the standard plethysmograph can be derived by observing that the detected intensity signal 1300 is merely an out of phase version of the absorption profile 1270. That is, the peak detected intensity 1372 occurs at minimum absorption 1272 (FIG. 12), and minimum detected intensity 1374 occurs at maximum absorption 1274 (FIG. 12). Further, a rapid rise in absorption 1276 (FIG. 12) during the inflow phase of the plethysmograph is reflected in a rapid decline 1376 in intensity, and the gradual decline 1278 (FIG. 12) in absorption during the outflow phase of the plethysmograph is reflected in a gradual increase 1378 in detected intensity.

Figure 14:
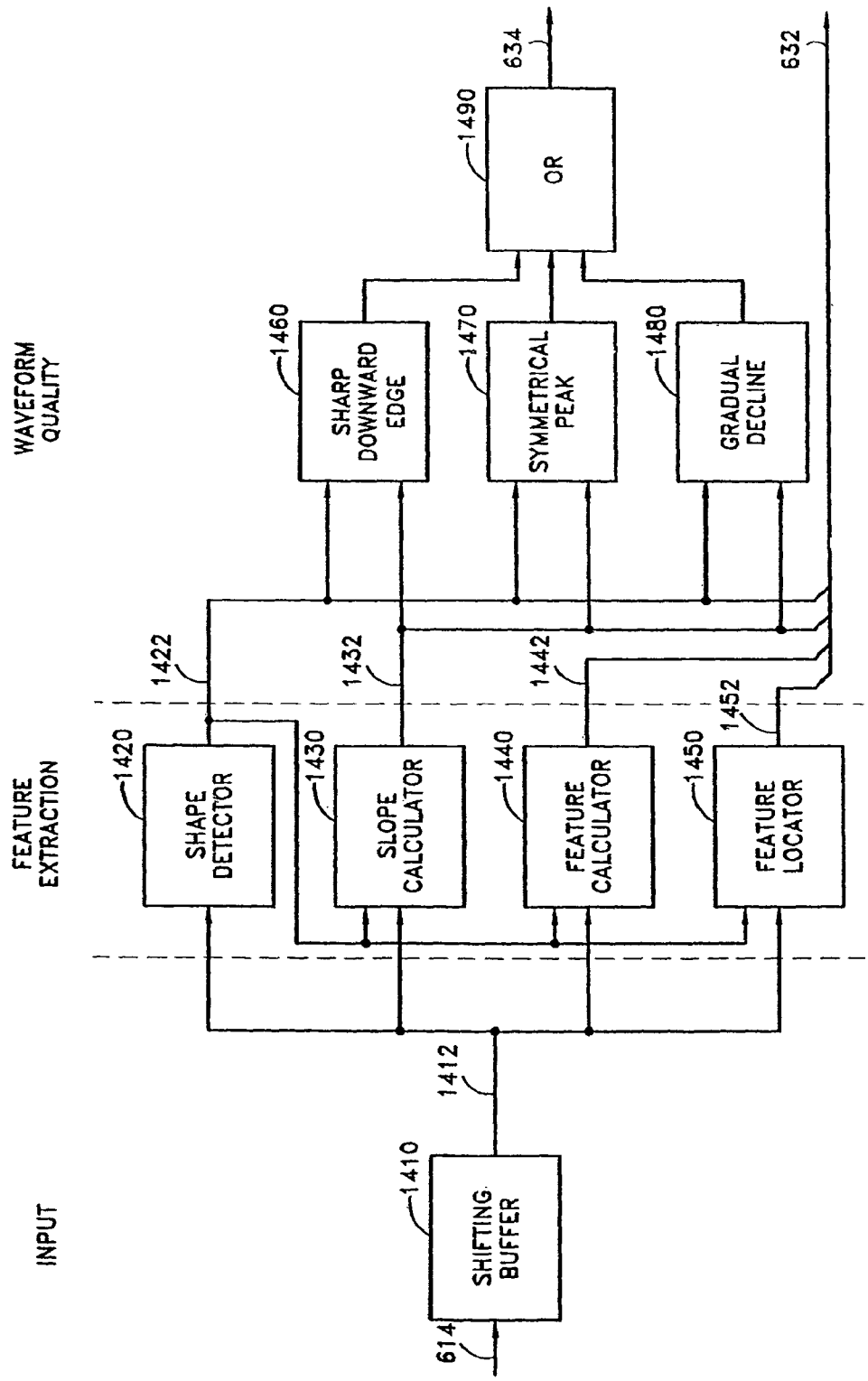
FIG. 14 is a functional block diagram of the plethysmograph feature extraction signal processing.

FIG. 14 illustrates the digital signal processing for plethysmograph feature extraction 630 (FIG. 6). The input 614 is the IR signal output from the demultiplexer 710 (FIG. 7). This signal is shifted into a first-in, first-out (FIFO) buffer, which allows fixed-length portions of the input signal 614 to be processed for feature extraction. The buffered output signal 1412 is coupled to a shape detector 1420, slope calculator 1430, feature width calculator 1440 and a notch locator 1450, which perform the core feature extraction functions. The shape detector 1420 determines if a particular buffered signal portion 1412 contains specific gross features, such as a peak, a valley, an upward slope, a downward slope, a dicrotic notch or a multiple dicrotic notch. A detected shape output 1422 containing one or more flags indicating the gross feature content of the current signal portion 1412 is coupled to the other feature extraction functions 1430, 1440, 1450 and to the waveform quality determination functions 1460, 1470, 1480. A slope calculator 1430 determines the amount of positive or negative slope in the signal portion 1412 if the shape detector output 1422 indicates a slope is present. The output slope value 1432 is coupled to the waveform quality functions 1460, 1470, 1480 in addition to the feature extraction output 632. A feature calculator 1440 quantifies a feature in one or more signal portions 1412 specified by the shape detector 1420, such as the magnitude, the area under, or the width of a peak or notch. The feature calculator output 1442 is a code indicating the feature and its value, which is coupled to the feature extraction output 632. A feature locator 1450 quantifies the time of occurrence of one or more features of a signal portion 1412 as specified by the shape detector 1420. The feature locator output 1452, which is coupled to the feature extraction output 632, is a code indicating a feature and an associated code indicating time of occurrence in reference to a particular epoch. The feature locator output 1452 allows a determination of the relative location of plethysmograph features in addition to a phase comparison of plethysmographs derived from two or more tissue sites. Another feature extraction output 634, which is coupled to the multiple parameter processor 640 (FIG. 6), provides an indication of waveform quality. Input signals portions 1412 not having either a sharp downward edge 1460, a symmetrical peak 1470 or a gradual decline 1480 are not processed further.

Multiple Parameter Processor

Figure 15:
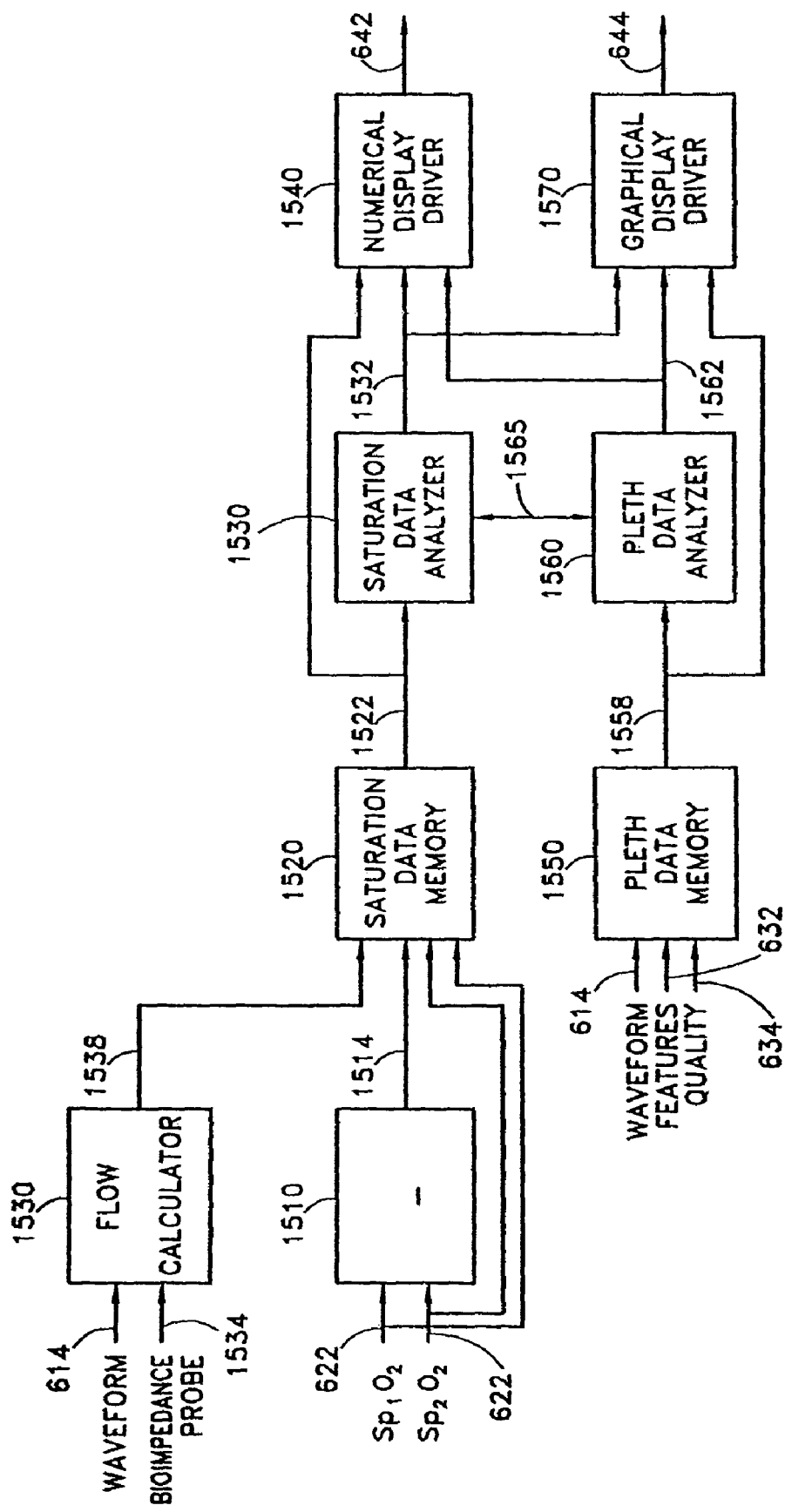
FIG. 15 is a functional block diagram of the multiple parameter signal processing.

FIG. 15 illustrates the multiple parameter processing portion 640 (FIG. 6) of the signal processing. A differencing function 1510 has as inputs a first saturation value, $Sp_1O_2$, and a second saturation value, $Sp_2O_2$, 622. The saturation input values 622 can be arterial and venous saturation values from a single data channel, arterial saturation values from two different data channels or venous saturation values from two different data channels. The differences of the saturation value inputs 622 are provided as an output 1514, which is coupled to a saturation data memory 1520. The saturation values 622 are also directly coupled to the saturation data memory 1520. The memory 1520 stores a record of saturation values, $SpO_2$, for each channel, delta saturation values, $\Delta$sat, for each channel and cross-channel delta saturation values, $\Delta sat_{xy}$, as required for a particular application. A flow calculator 1530 utilizes a plethysmograph input 614 or a bioimpedance probe input 1534 to provide a flow value 1538, which is also coupled to the saturation data memory 1520. For example, the flow value 1538 may be a perfusion index, PI, defined as follows:

$$PI = \frac{IR_{max} - IR_{min}}{IR_{DC}} \quad (11)$$

where $IR_{max}$ is the maximum value, $IR_{min}$ is the minimum value, and $IR_{DC}$ is the average value of the IR plethysmograph signal 614 (FIG. 7).

The saturation data memory 1520 provides a buffered output 1522 that is coupled to a numerical display driver 1540. The numerical display driver 1540 provides an output 642 to a standard display, such as LED or LCD numerical display modules or a CRT monitor. The memory output 1522 is also coupled to a saturation data analyzer 1530, one function of which calculates a long-term trend of the values in memory 1520. For example, the saturation data analyzer may average a saturation value over time, or provide samples of the saturation values taken at regular time intervals. The output 1532 can either be numerical, which is coupled to the numerical display driver 1540, or graphical, which is coupled to the graphical display driver 1570. The graphical display driver 1570 provides an output 644 to a standard graphical display device, such as LED or LCD graphical display modules or a CRT monitor.

A pleth data memory 1550 has as inputs the IR plethysmograph signals 614 (FIG. 7) from each data channel and the associated extracted features 632 (FIG. 14). The memory 1550 also has an input indicating waveform quality 634 (FIG. 14). The pleth memory 1550 provides a buffered output 1558 that is coupled to the graphical display driver 1570, allowing display of the plethysmograph waveforms for each data channel. The memory output 1558 is also coupled to a pleth data analyzer 1560, one function of which calculates a long-term trend of the plethysmograph and shape parameters in pleth memory 1520. For example, the pleth data analyzer 1560 may provide an average of particular shape parameters over time. As another example, the pleth data analyzer 1560 may provide a graphic showing an accumulation of many overlaid plethysmographs. The output 1562 can either be numerical, which is coupled to the numerical display driver 1540, or graphical, which is coupled to the graphical display driver 1570.

Another function of the saturation data analyzer 1530 and the pleth data analyzer 1560 is to compare oxygen status and plethysmograph parameters derived from multiple sites in order to isolate noise artifacts and to derive a more accurate estimate of these parameters. For example, it is unlikely that motion artifact will affect each peripheral site in the same manner. If the quality input 634 indicates a noisy plethysmograph for one channel during a particular time period, the pleth data analyzer 1560 can exchange this information 1565 with the saturation data analyzer 1530. The saturation data analyzer 1530 can then ignore the saturation data for that channel for that time period in lieu of saturation data from another channel. In a similar fashion, noisy data from multiple channels can be averaged, correlated or otherwise processed to provide an estimate of $Sp_aO_2$, $Sp_vO_2$ or pulse rate, or to provide a plethysmograph that is more accurate than can be derived from a single data channel.

FIG. 16A illustrates detail of a single-site display screen 180 for the stereo pulse oximeter. The display has a numerical display portion 1610 controlled by the numerical display driver 1540 (FIG. 15) and a graphical display portion 1660 controlled by the graphical display driver 1570 (FIG. 15). The numerical display portion 1610 displays a value for $Sp_aO_2$ 1620, $Sp_vO_2$ 1630 and pulse rate 1640 for a particular tissue site. The graphical display portion 1660 displays a plethysmograph 1662 for the corresponding tissue site, which can be displayed as a single waveform or an accumulated multiple of overlayed waveforms that may reveal a waveform trend. A push button or menu selection allows the user to switch to a display of data from any single one of the multiple tissue sites to which a sensor is attached.

Figure 16B:
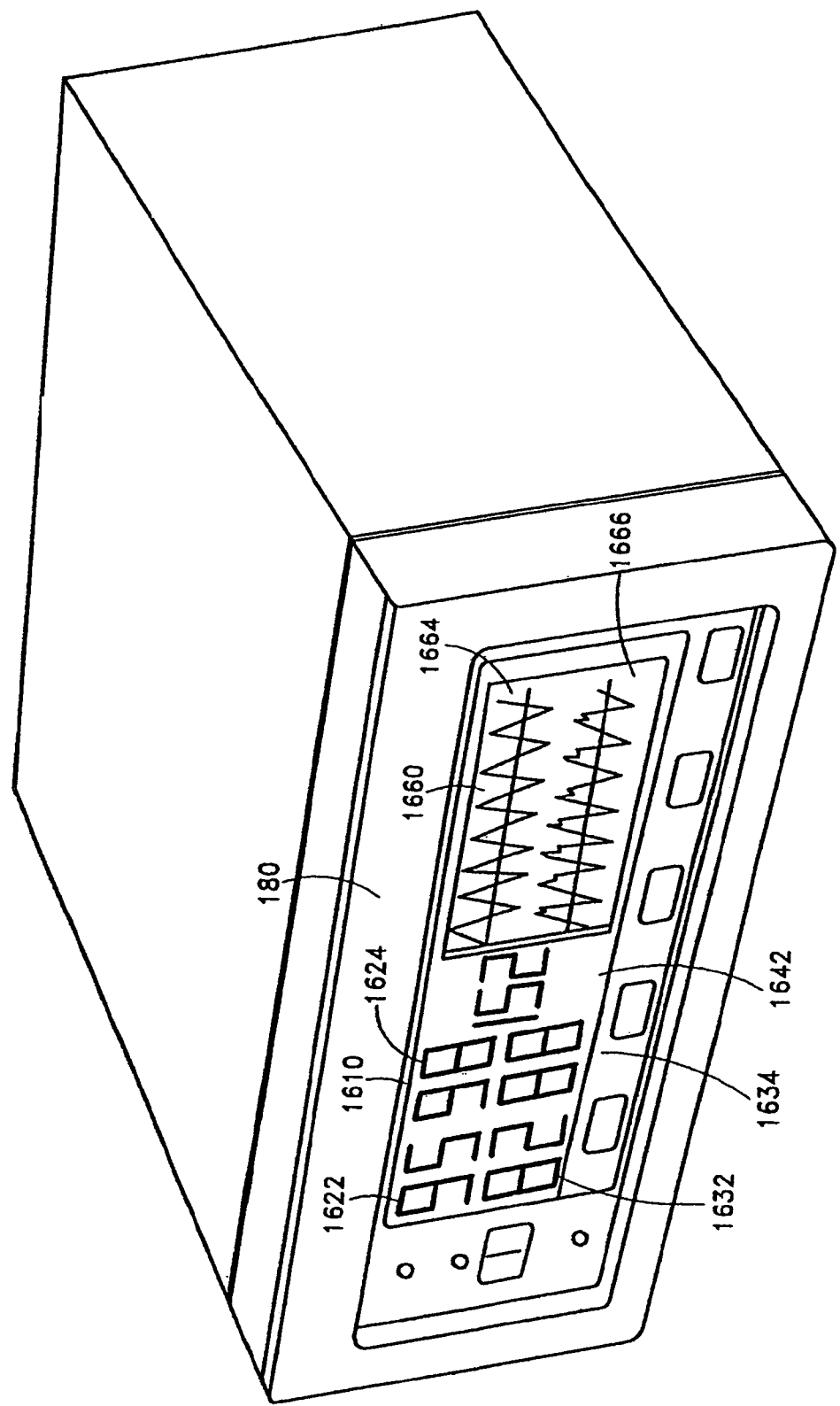
FIG. 16B is an illustration of a multi-site stereo pulse oximeter display screen.

FIG. 16B illustrates detail of a multi-site display screen 180 for the stereo pulse oximeter. The numerical display portion 1610 displays a value for $Sp_aO_2$ 1622 and $Sp_vO_2$ 1632 for a first tissue site. Also displayed is a value for $Sp_aO_2$ 1624 and $Sp_vO_2$ 1634 for a second tissue site. In addition, a value for pulse rate 1642 derived from either the first or second tissue site, or both, is displayed. The graphical display portion 1660 displays a first plethysmograph 1664 and a second plethysmograph 1666 corresponding to the first and second tissue sites, respectively. A push button, menu selection allows the user to manually switch between the single site display (FIG. 16A) and the multi-site display (FIG. 16B). Also, a triggering event, such as an alarm based on multiple-site oxygen status parameters, causes the display to automatically switch from the single-site display to the multi-site display, enabling the user better view the conditions that caused the triggering event.

One of ordinary skill will appreciate many display screens variations from those shown in FIGS. 16A and 16B that are within the scope of this invention. For example, the stereo pulse oximeter could be configured to provide several push button or menu selectable display screens. One display screen might display more than two channels of oxygen status data. Another display screen could display cross-channel parameters such as $\Delta sat_{xy}$, or a comparison of plethysmograph shape parameters from two channels. One of ordinary skill will also appreciate many variations and modifications of layout and design for the graphical and numerical displays within the scope of this invention.

Stereo Pulse Oximetry Applications

Oxygen Titration

Oxygen is one of the most commonly used drugs in an intensive care unit and is an integral part of all respiratory support. The goal of oxygen therapy is to achieve adequate delivery of oxygen to the tissues without creating oxygen toxicity. Too little oxygen results in organ damage and, in particular, brain damage. Too much oxygen can result in, for example, pulmonary edema and, in neonates, retinopathy of prematurity (ROP). Infants receiving oxygen therapy, in particular, must have inspired oxygen concentration and blood oxygen levels monitored closely.

Oxygen titration in neonates is currently accomplished with either transcutaneous monitoring or monitoring with a conventional pulse oximeter. As mentioned above, transcutaneous monitoring involves the placement of a heated Clark electrode against the skin surface. The electrode is secured to the skin surface with an airtight seal to eliminate contamination by room air gases. The skin surface beneath the electrode is then heated, which opens pre-capillary sphincters allowing localized arteriolar blood flow beneath the sensor. The so-called $T_cO_2$ value that is measured correlates well with $P_aO_2$. However, there are several drawbacks to this approach. Because the skin surface must be heated, a fifteen minute elapsed time after application is necessary before stable readings are acquired. Further, the required temperature is 43-45° C. (110° F.), with an associated risk of burns. In addition, titration is often accomplished by simply maintaining $T_cO_2$ within acceptable limits for this parameter, e.g. an equivalent $P_aO_2$ of 50-80 mm Hg for neonates. However, $P_aO_2$ alone does not provide an indication of balance between inspired oxygen and the rate of tissue oxygen consumption. If the patient is particularly anemic or hypovolemic, has an abnormal hemoglobin, or a small cardiac output, then oxygen delivery may be inadequate even in the presence of a normal $P_aO_2$. Titration with a conventional pulse oximeter is similarly accomplished by maintaining $Sp_aO_2$ within acceptable limits, which also fails to consider tissue oxygen consumption.

Oxygen titration can be more adequately monitored with a continuous indication of oxygen consumption, which is equal to oxygen delivery according to Fick's algorithm, as noted above. Further, continuous monitoring of oxygen consumption at a peripheral tissue site, although not necessarily indicative of overall oxygen consumption, may be indicative of an oxygen supply dependency. A measure of peripheral oxygen consumption can be expressed in terms of $\Delta sat = Sp_aO_2 - Sp_vO_2$ and perfusion, which, as noted above, are parameters advantageously provided by the stereo pulse oximeter according to the present invention. Oxygen consumption at a peripheral site is obtained by multiplying the difference between peripheral arterial and venous oxygen content by perfusion at the site.

$$VpO_2 = [O_2 \text{ content (arterial)} - O_2 \text{ content (venous)}]\Phi \quad (12)$$

where oxygen content is measured in milliliters (ml) of $O_2$ per deciliters (dl) of blood and $\Phi$ denotes perfusion in deciliters per minute. Oxygen content, however, can be expressed in terms of the amount of oxygen bound to the hemoglobin plus the amount of oxygen dissolved in the plasma. The amount of bound oxygen is equal to the hemoglobin concentration, $C_{hb}$, in grams per deciliter of blood, times the hemoglobin carrying capacity, which is 1.34 milliliters of $O_2$ per gram of hemoglobin times the hemoglobin oxygen saturation, $SO_2$. The amount of dissolved oxygen is simply the partial pressure of oxygen, $PO_2$, times the $O_2$ solubility coefficient in blood, which is 0.003 milliliters of $O_2$ per deciliter. The sum of these two terms yields:

$$O_2 \text{ content} = 1.34 C_{Hb} SO_2 + 0.003 PO_2 \quad (13)$$

Substituting equation (13) into equation (12) yields the following equation for tissue oxygen consumption:

$$VpO_2 = [1.34 C_{Hb}(Sp_aO_2 - Sp_vO_2) + 0.003(P_aO_2 - P_vO_2)]\Phi \quad (14)$$

Except when the fractional inspired oxygen, $FiO_2$, is high, blood plasma plays a minimal role in oxygen delivery. Thus, peripheral oxygen consumption is approximately:

$$VpO_2 = [1.34 C_{Hb} \Delta sat]\Phi \quad (15)$$

In order to illustrate a schema of oxygen titration, it is convenient to characterize the relationship between oxygen supplied at the airway to oxygen consumed at a peripheral tissue site. Specifically, characterization of the relationship between $\Delta sat$, $\Phi$ and $FiO_2$ is useful. Assuming constant oxygen consumption at the tissue site, equation (15) is:

$$\Delta sat \, \Phi = \text{constant} \quad (16)$$

Equation (16) has a simple analog in electronic circuits, i.e. a variable resistor across a current or voltage source adjusted to maintain constant power. In this analog circuit, the current through the resistor, I, is equivalent to perfusion, the voltage across the resistor, V, is equivalent to $\Delta sat$ and the constant of equation (16) is equivalent to the constant power, P, consumed by the resistor. The equation representing this electrical analog is:

$$V \times I = P \quad (17)$$

Figure 17A:
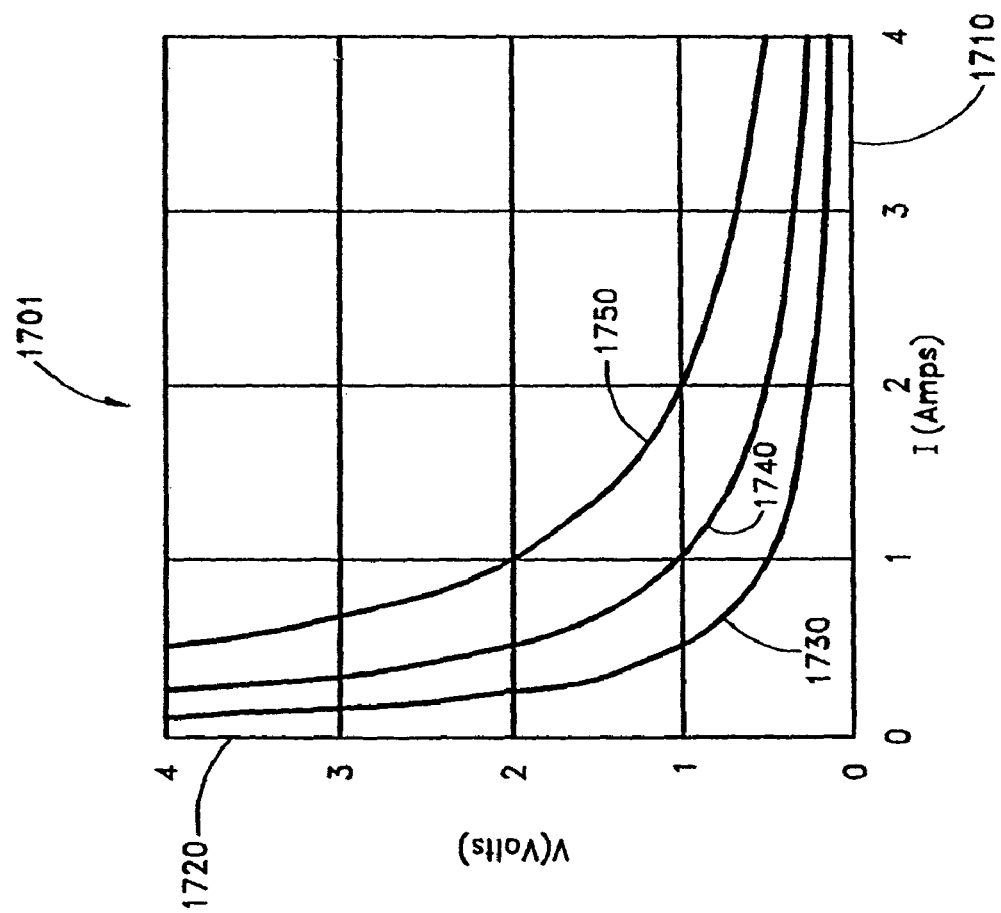
FIG. 17A is a graph depicting a family of constant power curves for the electrical analog of constant oxygen consumption.

FIG. 17A shows a graph 1701 that depicts a family of curves each corresponding to different values of P in equation (17). The graph 1701 has an x-axis 1710 indicating current, I, and a y-axis 1720 indicating voltage, V. A first curve 1730 shows V versus I for a constant power, P, of 0.5 watts; a second curve 1740 shows V versus I for a constant P of 1 watt; and a third curve 1750 shows V versus I for a constant P of 2 watts. Using the analogy between equations (16) and equation (17), whenever $\Phi$ (current) is small, the $\Delta sat$ (voltage) is large and vice-a-versa. Also, a change in consumption (power) causes a shift in the curve along with a change in its curvature. That is, if the body suddenly changes its metabolic rate at the peripheral tissue site, the curve will accordingly shift up or shift down and will change its shape. Equation (16) and the analogous constant consumption curves of FIG. 17A assume a supply independent condition, i.e. that peripheral oxygen consumption is satisfied by peripheral oxygen delivery. If the peripheral tissue site is starved for oxygen, then the locus of points for Δsat versus Φ is quite different from a hyperbola The amount of tissue oxygen extraction is at a maximum and is independent of Φ. Accordingly Δsat is at a maximum and independent of Φ. The above analysis provides insight into the relationship between Δsat and Φ. The relationship between Δsat and $FiO_2$ can also be characterized.

Figure 17B:
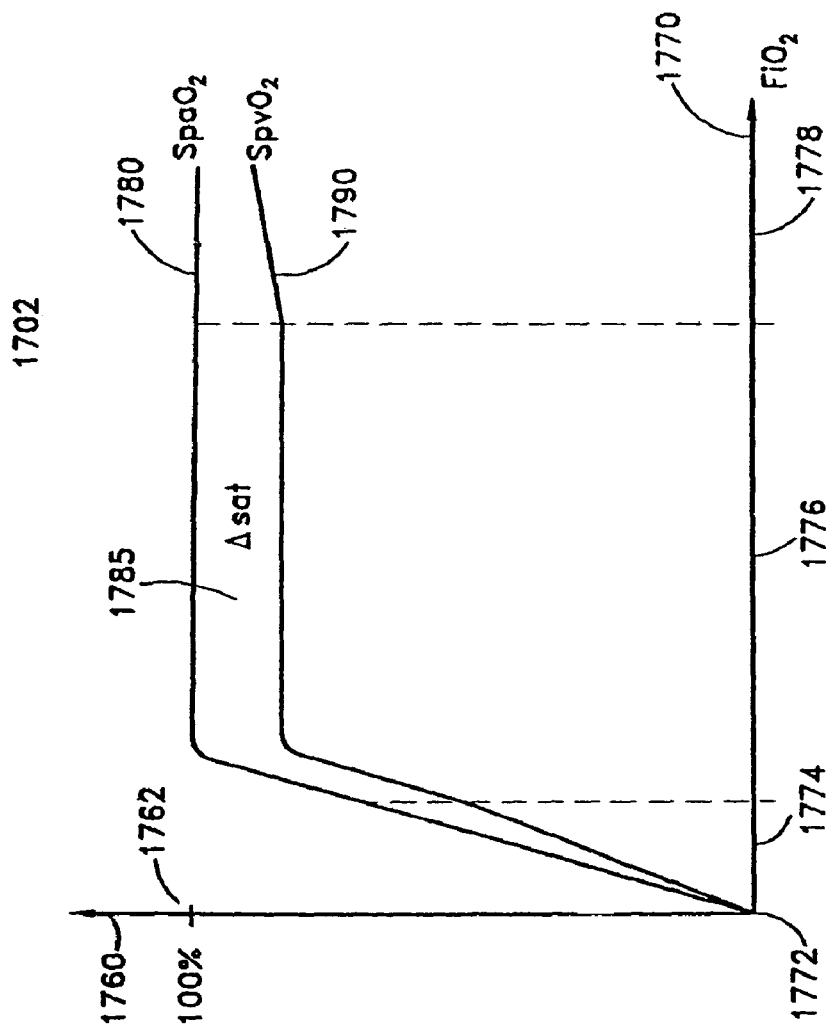
FIG. 17B is a graph depicting arterial and venous oxygen saturation versus fractional inspired oxygen.

FIG. 17B shows a graph 1702 of saturation along a y-axis 1760 and fractional inspired oxygen along an x-axis 1770. A curve of $Sp_aO_2$ 1780 and a curve of $Sp_vO_2$ 1790 are depicted versus $FiO_2$. The difference between these curves 1780, 1790 yields Δsat 1785 versus $FiO_2$. When $FiO_2$ is zero 1772, oxygen saturation and, hence, both $Sp_aO_2$ 1780 and $Sp_vO_2$ 1790 are zero. As $FiO_2$ is increased, $Sp_aO_2$ 1780 also increases until virtually reaching 100 percent saturation 1762. As $FiO_2$ increases further, $Sp_aO_2$ 1780 stays at virtually 100 percent saturation 1762. As $FiO_2$ is increased from zero 1772, $Sp_vO_2$ 1790 also increases. In this low $FiO_2$ region 1774, the peripheral tissue site is supply dependent and Δsat 1785 also increases. At a certain point, the tissue site oxygen demand is met by supply. In this supply independent region 1776, oxygen consumption is constant and equation (16) is valid. Also, Δsat 1785 is at a constant maximum, which is a function of the metabolism at the tissue site. As $FiO_2$ increases further, eventually the partial pressure of oxygen becomes significant and the second term of equation (14) must be considered. In this high $FiO_2$ region 1778, Δsat 1785 decreases because some of the tissue oxygen consumption is supplied by oxygen dissolved in the plasma.

Figure 17C:
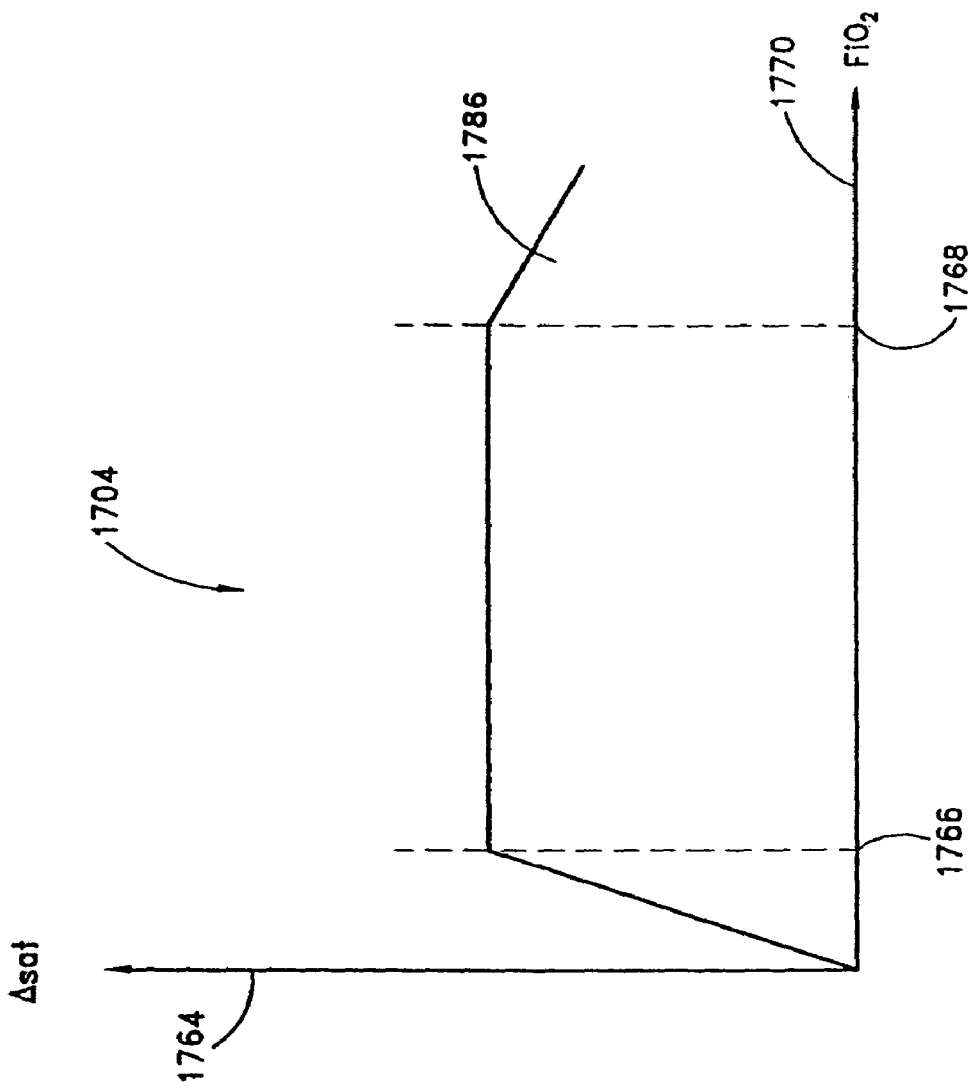
FIG. 17C is a graph depicting arterial minus venous oxygen saturation versus fractional inspired oxygen.

FIG. 17C shows a graph 1704 of saturation difference along a y-axis 1764 and fractional inspired oxygen along an x-axis 1770. A curve of Δsat 1786 is depicted versus $FiO_2$, corresponding to the region Δsat 1785 depicted in FIG. 17B. The curve 1786 has a first deflection point 1766 occurring at the transition between the low $FiO_2$ region 1774 (FIG. 17B) and the supply independent region 1776 (FIG. 17B). The curve 1786 also has a second deflection point 1768 occurring at the transition between the supply independent region 1776 (FIG. 17B) and the high $FiO_2$ region 1778 (FIG. 17B). The curve 1786 illustrates how the trend for Δsat, as measured by the stereo pulse oximeter, can be used to accurately titrate oxygen. The goal of oxygen titration is to supply sufficient oxygen to supply tissue demand and avoid unnecessarily high amounts of $FiO_2$. Thus, the Δsat parameter should be monitored so that $FiO_2$ is adjusted between the two deflection points 1766, 1768. For neonates, $FiO_2$ should be adjusted just beyond the first deflection point 1766. For adults, $FiO_2$ should be adjusted just before the second deflection point 1768.

Figure 18:
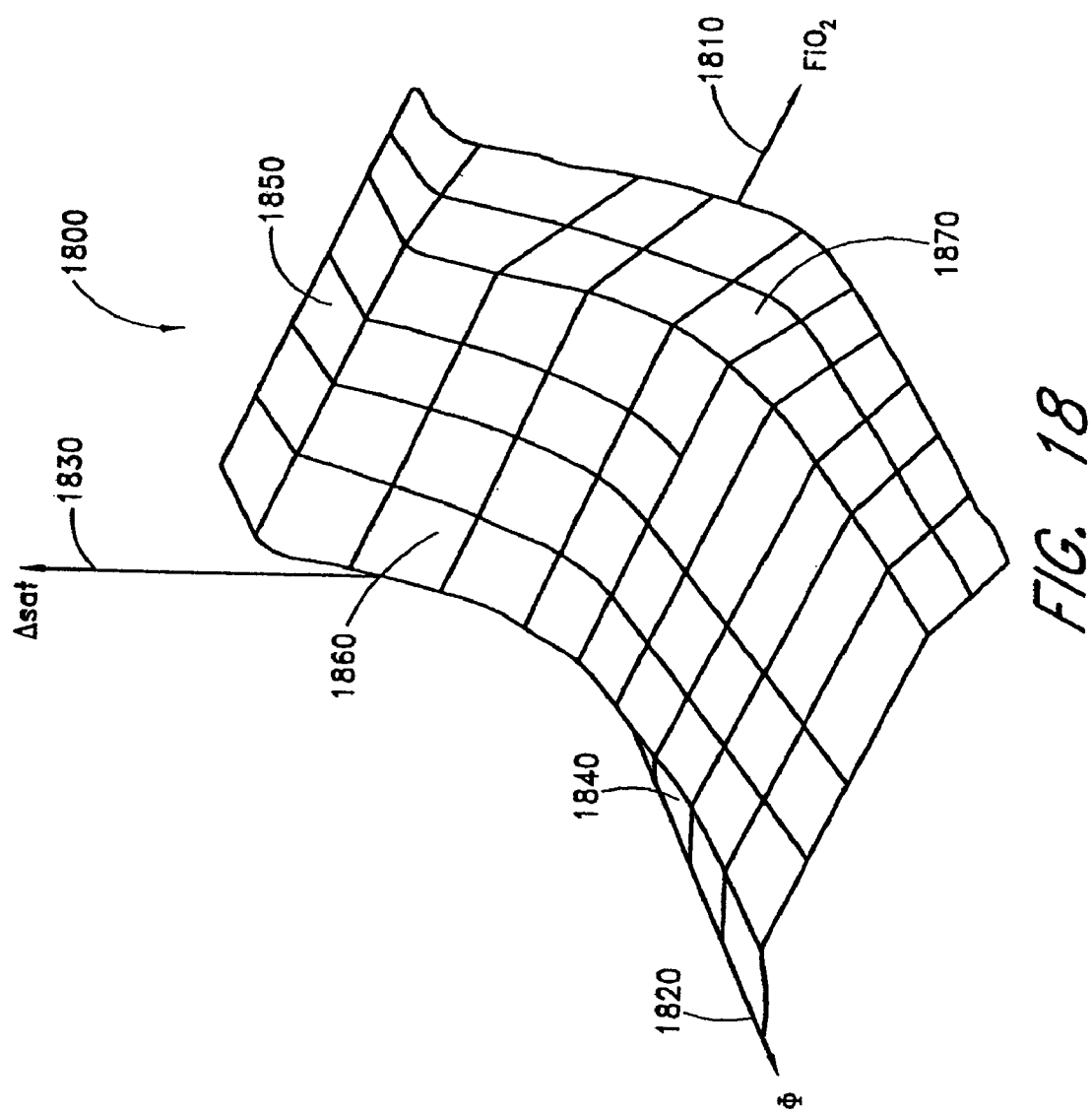
FIG. 18 is a three-dimensional graph depicting a delta oxygen saturation surface.

FIG. 18 illustrates a graph having a three-dimensional surface 1800 generally depicting the relationship between Δsat, Φ and $FiO_2$ from the combined graphs of FIGS. 17A and 17C. The graph has an x-axis 1810 showing $FiO_2$, a y-axis 1820 showing Φ and a z-axis 1830 showing Δsat. The surface 1800 has a supply dependent region 1840, a perfusion-limited region 1850, a constant consumption region 1860 and a plasma dependent region 1870. The surface describes the oxygen status of a peripheral tissue site. The supply dependent region 1840 corresponds to the low $FiO_2$ region 1774 (FIG. 17B) described above. That is, inspired oxygen into the lungs is so low that, at the tissue site, oxygen extraction by the tissues is limited by oxygen delivery, and Δsat falls rapidly as $FiO_2$ is reduced. The perfusion-limited region 1850 along the x-axis 1810 represents a low perfusion state where equation (16) is not valid. That is, perfusion at the tissue site is so low that oxygen extraction by the tissues is at a maximum, and, hence, Δsat is at a maximum and is independent of $FiO_2$. A cross-section of the surface taken parallel to the y-axis 1820 yields a hyperbole-shaped constant consumption region 1860, consistent with the constant metabolic rate curves illustrated above with respect to FIG. 17A. The plasma dependent region 1870 corresponds to the high $FiO_2$ region 1778 (FIG. 17B) described above. That is, inspired oxygen into the lungs is so high that the tissue site is partially dependent on oxygen dissolved in the plasma The surface 1800 illustrates that perfusion should be monitored simultaneously with Δsat to avoid the perfusion-limited region 1850, where Δsat is an unresponsive indicator of $FiO_2$, and to avoid misinterpreting hyperbolic changes in Δsat that result from changes in perfusion.

Persistent Pulmonary Hypertension in Neonates

Figure 19:
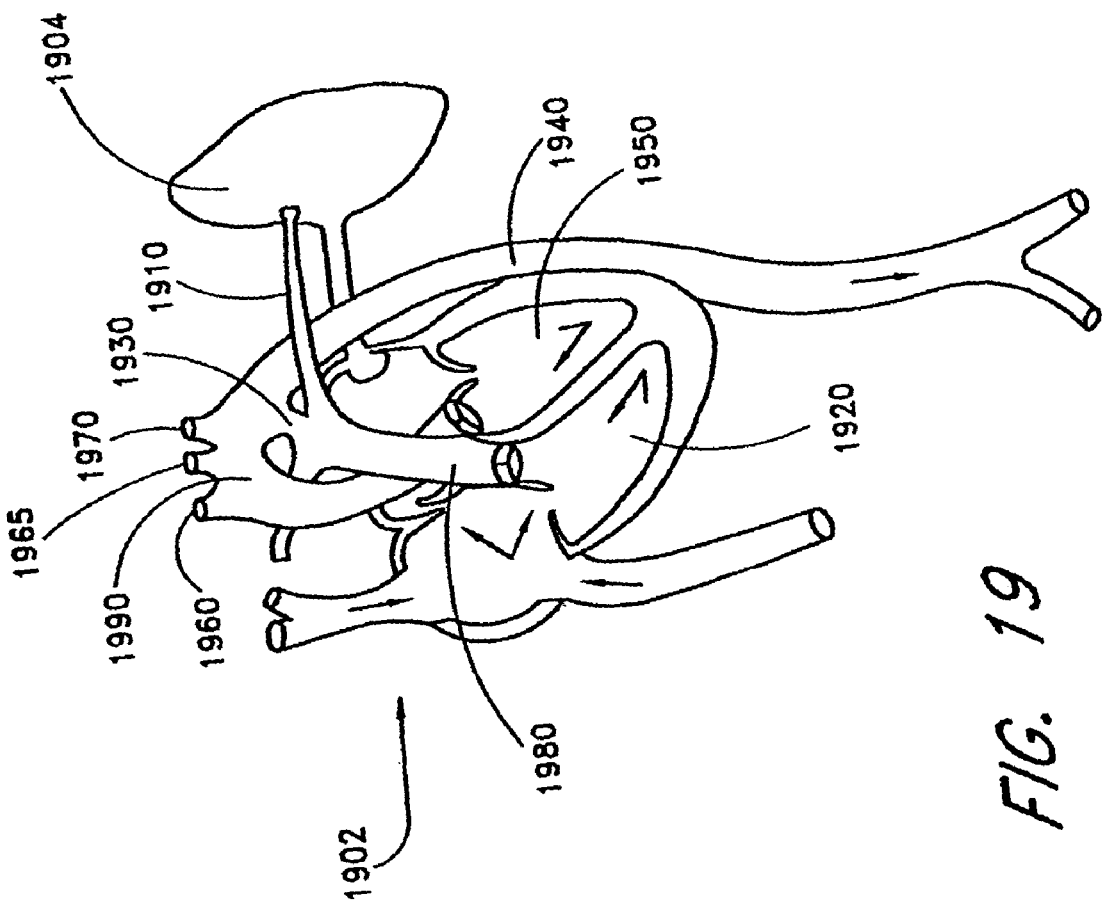
FIG. 19 is an illustration of a neonatal heart depicting a pulmonary hypertension condition.

FIG. 19 illustrates the heart/lung circulation of a hypertensive neonate. Persistent Pulmonary Hypertension in Neonates (PPHN) is a neonatal condition with persistent elevation of pulmonary vascular resistance and pulmonary artery pressure. Shown is a neonatal heart 1902 and a portion of a neonatal lung 1904. The pulmonary artery 1910 that normally feeds oxygen depleted "blue" blood from the right ventricle 1920 to the lung 1904 is constricted. The back pressure from the constricted artery 1910 results in a right-to-left shunting of this oxygen depleted blood through the ductus arteriosus 1930, causing it to mix with oxygen rich "red" blood flowing through the descending aorta 1940. PPHN treatment options include vasodilators, such as nitric oxide (NO). Inhaled exogenous NO causes a dose-dependent decrease in pulmonary artery pressure and pulmonary vascular resistance, as well as a parallel increase in pulmonary blood flow, without affecting systemic arterial pressure. However, the response to NO therapy is a function of the cause of the PPHN as well as the time elapsed before initiation of therapy. Potential toxic effects of NO dictate the proper titration of NO gas. Too little NO may not effectively relieve pulmonary hypertension, and too much NO may cause cellular injury or toxicity. NO therapy is currently monitored using intermittent ultrasound imaging and/or in vitro blood gas measurements. The drawbacks to these techniques are noncontinuous monitoring and disturbances to the neonate that can exacerbate or not reflect the hypertension in the non-disturbed state.

The stereo pulse oximeter according to the present invention allows noninvasive, continuous monitoring of a neonate for detection and managed treatment of PPHN that does not disturb the patient. A right hand sensor 130 (FIG. 1) provides arterial oxygen saturation and a plethysmograph for blood circulating from the left ventricle 1950 through the innominate artery 1960, which supplies the right subclavian artery. Because the innominate artery 1960 is upstream from the shunt at the ductus arteriosus 1930, the oxygen saturation value and plethysmograph waveform obtained from the right hand are relatively unaffected by the shunt and serve as a baseline or reference for comparison with readings from other tissue sites. Alternatively, a reference sensor can be placed on a facial site, such as an ear, the nose or the lips. These sites provide arterial oxygen saturation and a plethysmograph for blood circulating from the left ventricle 1950 to the innominate artery 1960, which supplies the right common carotid artery (not shown), or to the left common carotid artery 1965.

A foot sensor 120 (FIG. 1) provides oxygen status for blood supplied from the descending aorta 1940. The shunt 1930 affects both the oxygen saturation and the blood flow in the descending aorta 1940. As stated above, the shunt 1930 causes oxygen-depleted blood to be mixed with oxygen-rich blood in the descending aorta 1940. Because the descending aorta 1940 supplies blood to the legs, the oxygen saturation readings at the foot will be lowered accordingly. The PPHN condition, therefore, is manifested as a higher arterial oxygen saturation at the right hand reference site and a lower saturation at the foot site.

The shunt also allows a transitory left to right flow during systole, which distends the main pulmonary artery 1980 as the result of the blood flow pressure at one end from the right ventricle and at the other end from the aortic arch 1990. A left-to-right flow through the shunt 1930 into the distended artery 1980 alters the flow in the descending aorta 1940 and, as a result, the plethysmograph features measured at the foot. The PPHN condition, therefore, also is manifested as a plethysmograph with a narrow peak and possibly a well-defined dicrotic notch at the left hand baseline site and a broadened peak and possibly no notch at the foot site.

An optional left hand sensor 110 (FIG. 1) provides oxygen status for blood circulating from the left ventricle through the left subclavian artery 1970 that supplies the left arm. Because the left subclavian artery 1970 is nearer the shunt 1930 than the further upstream innominate artery 1960, it may experience some mixing of deoxygenated blood and an alteration in flow due to the shunt 1930. The PPHN condition, therefore, may also be manifested as a reduced saturation and an altered plethysmograph waveform at the left hand site as compared with the right hand baseline site, although to a lesser degree than with a foot site. Thus, the PPHN condition can be detected and its treatment monitored from Δsat and plethysmograph morphology comparisons between a right hand baseline sensor site and one or more other sites, such as the left hand or foot.

Patent Ductus Arteriosus

Figure 20:
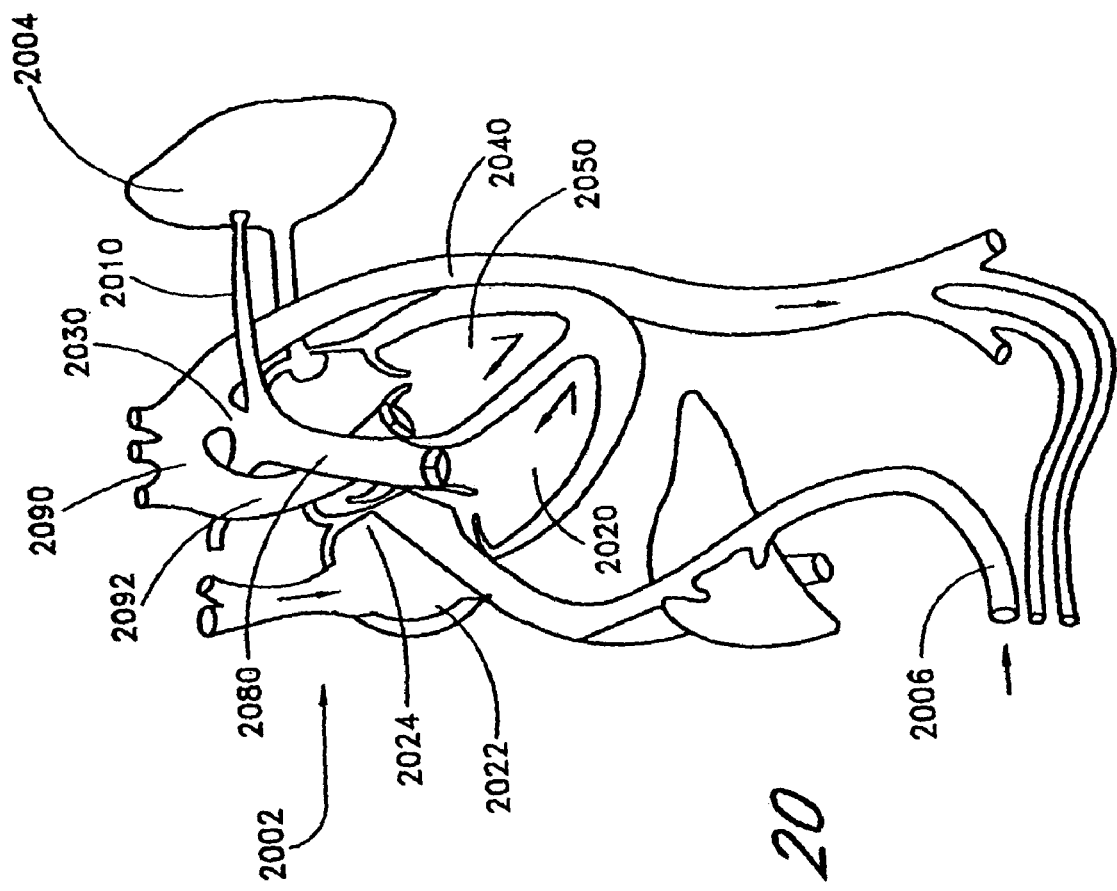
FIG. 20 is an illustration of a fetal heart depicting the ductus arteriosis.

FIG. 20 illustrates the fetal heart/lung circulation. Shown is a fetal heart 2002 and a portion of a fetal lung 2004. The lung 2004 is non-functional and fluid-filled. Instead, oxygenated blood is supplied to the fetus from gas-exchange in the placenta with the mother's blood supply. Specifically, oxygenated blood flows from the placenta, through the umbilical vein 2006 and into the right atrium 2022. There, it flows via the foramen 2024 into the left atrium 2052, where it is pumped into the left ventricle 2050 and then into the aortic trunk 2092. Also, oxygenated blood is pumped from the right atrium 2022 into the right ventricle 2020 and directly into the descending aorta 2040 via the main pulmonary artery 2080 and the ductus arteriosus 2030. Normally, the ductus arteriosus 2030 is only open (patent) during fetal life and the first 12 to 24 hours of life in term infants. The purpose of the ductus arteriosus 2030 is to shunt blood pumped by the right ventricle 2020 past the constricted pulmonary circulation 2010 and into the aorta 2040.

Figure 21:
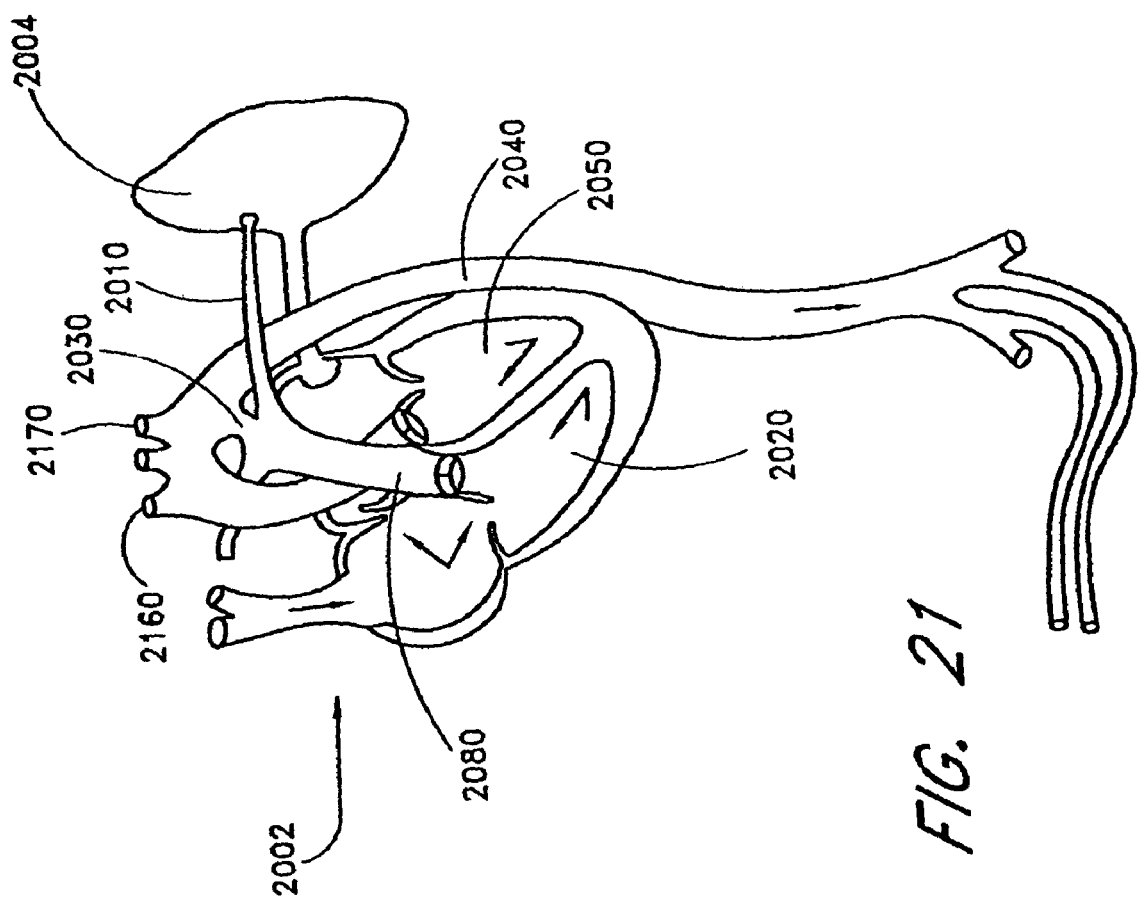
FIG. 21 is an illustration of a neonatal heart depicting a patent ductus arteriosis (PDA).

FIG. 21 illustrates a neonatal heart 2002 with a patent ductus arteriosus 2030. The ductus arteriosus frequently fails to close in premature infants, allowing left-to-right shunting, i.e. oxygenated "red" blood flows from the aorta 2040 to the now unconstricted pulmonary artery 2010 and recirculates through the lungs 2004. A persistent patent ductus arteriosus (PDA) results in pulmonary hyperperfusion and an enlarged right ventricle 2020, which leads to a variety of abnormal respiratory, cardiac and genitourinary symptoms. Current PDA diagnosis involves physical examination, chest x-ray, blood gas analysis, echocardiogram, or a combination of the above. For example, large PDAs may be associated with a soft, long, low-frequency murmur detectable with a stethoscope. As another example, two-dimensional, color Doppler echocardiography may show a retrograde flow from the ductus arteriosus 2030 into the main pulmonary artery 2080. Once a problematic PDA is detected, closure can be effected medically with indomethacin or ibuprofen or surgically by ligation. Multiple doses of indomethacin are commonplace but can still result in patency, demanding ligation. A drawback to current diagnostic techniques is that clinical symptoms of a PDA can vary on an hourly basis, requiring extended and inherently intermittent testing.

The stereo pulse oximeter according to the present invention allows for continuous evaluation of PDA symptoms using non-invasive techniques. A right hand sensor 130 (FIG. 1) provides arterial oxygen saturation and a plethysmograph for blood circulating from the left ventricle 2050 through the innominate artery 2160, which supplies the right subclavian artery leading to the right arm. Because the innominate artery 2160 is upstream from the shunt at the ductus arteriosus 2030, the oxygen saturation value and plethysmograph waveform obtained from the right hand are relatively unaffected by the shunt and serve as a baseline for comparison with readings from other tissue sites.

A foot sensor 120 (FIG. 1) provides oxygen status for blood supplied from the descending aorta 2040. Unlike a PPHN condition, the shunt 2030 does not affect oxygen saturation in the descending aorta 2040, because the relatively low pressure in the pulmonary artery 2010 does not allow a mixing of deoxygenated blood into the relatively high pressure flow of oxygenated blood in the aorta 2040. However, like a PPHN condition, the shunt 2030 does affect the aortic flow. In particular, the shunt allows a transitory left-to-right flow during systole from the high pressure aorta 2040 to the low pressure pulmonary circulation 2010. This left-to-right flow through the shunt 1930 alters the flow in the descending aorta 1940 and, as a result, the plethysmograph features measured at the foot. The PDA condition, therefore, is manifested as a normal plethysmograph with a characteristically narrow peak and well-defined dicrotic notch at the right-hand baseline site compared with a damped plethysmograph with a broadened peak and reduced or missing notch at the foot site. Further, the foot site waveform is phase shifted from the baseline waveform. These plethysmograph differences are accompanied by comparable arterial oxygen saturation values between the right-hand site and the foot site.

An optional left hand sensor 110 (FIG. 1) provides oxygen status for blood circulating from the left ventricle through the left subclavian artery 2170 that supplies the left arm. Because the left subclavian artery 2170 is nearer the shunt 2030 than the further upstream innominate artery 2160, it may experience some alteration in flow due to the shunt 2030. The PDA condition, therefore, may also be manifested as an altered plethysmograph waveform at a left hand site as compared with the right hand baseline site, although to a lesser degree than with a foot site. Thus, the PDA condition can be detected and its treatment monitored from $\Delta sat_{xy} \approx 0$ and plethysmograph morphology and phase comparisons between a right hand baseline sensor site and one or more other sites, such as the left hand or foot. One of ordinary skill will recognize that multiple site comparisons using the stereo pulse oximeter of the current invention may also be used to detect other cardiac abnormalities that cause mixing of oxygenated and deoxygenated blood, such as a ventricular hole or a patent foramen. Further, abnormal mixing of oxygenated and deoxygenated blood may also be manifested in measurements provided by the stereo oximeters other than $\Delta sat_{xy}$ and $\Delta pleth_{xy}$ as described above. For example, an inversion in Δsat at a particular tissue site, i.e., $Sp_vO_2$ being larger than $Sp_aO_2$ at that site, would indicate such an abnormal condition.

Aortic Coarctation

Coarctation of the aorta is a congenital cardiac anomaly in which obstruction or narrowing occurs in the distal aortic arch or proximal descending aorta. It occurs as either an isolated lesion or coexisting with a variety of other congenital cardiac anomalies, such as a PDA. If the constriction is preductal, lower-trunk blood flow is supplied predominantly by the right ventricle via the ductus arteriosus, and cyanosis, i.e. poorly oxygenated blood, is present distal to the coarctation. This can be detected by the stereo pulse oximeter from a comparison of $Sp_aO_2$ between an upper body and a lower body site. If the constriction is postductal, blood supply to the lower trunk is supplied via the ascending aorta Differential plethysmographs between the upper and lower extremities may not exist if the ductus is widely patent. If the ductus closes, however, this condition can be detected by the stereo pulse oximeter as a reduced amplitude and phase delay between the plethysmographs measured at a lower body site with respect to an upper body site.

The stereo pulse oximeter has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A patient monitoring method comprising:
   inputting sensor signals from at least two physiological sensors of a physiological monitor, the physiological sensors attached to tissue sites comprising two or more of at least a portion the left arm, right arm, left leg, right leg, head, and neck of a patient;
   generating data channels corresponding to each of the tissue sites based on the sensor signals;
   calculating signal quality for each of the data channels using one or more processors of the physiological monitor; and
   outputting a first oxygen status parameter or plethysmograph derived from at least one of the data channels based upon a comparison of the calculated signal qualities.

2. The patient monitoring method according to claim 1 further comprising, using the one or more processors:
   selecting a low noise one of the data channels based upon the calculated signal qualities; and
   deriving the oxygen status parameter from the selected data channel during a particular time period.

3. The patient monitoring method according to claim 1 further comprising, using the one or more processors, deriving the oxygen status parameter from a combination of noisy data channels according to the signal quality calculations.

4. The patient monitoring method of claim 1, wherein the tissue sites include a right hand and a left hand of the patient.

5. The patient monitoring method of claim 1, wherein the tissue sites include a hand of the patient and a foot of the patient.

6. The patient monitoring method of claim 1, wherein the tissue sites include an upper body extremity and a lower body extremity.

7. The patient monitoring method of claim 1, wherein the first oxygen status parameter or plethysmograph is derived from one of the data channels, the method further comprising, using the one or more processors:
   comparing the first oxygen status parameter or plethysmograph with a second oxygen status parameter or plethysmograph derived from another of the data channels; and
   determining the presence of an abnormal health condition of the patient based upon the comparison.

8. The patient monitoring method of claim 7, wherein the abnormal health condition comprises a heart abnormality.

9. The patient monitoring method of claim 7, wherein the first and second oxygen status parameters or plethysmographs comprise first and second oxygen saturation values and the comparing comprises calculating a difference between the first and the second oxygen saturation values.

10. The patient monitoring method of claim 9, wherein determining comprises determining the presence of the abnormal health condition where the difference between the first and second oxygen saturation values is greater than a threshold amount.

11. A patient monitoring method, comprising:
    inputting sensor signals from at least two physiological sensors of a physiological monitor, the physiological sensors attached to tissue sites of a plurality of appendages of a patient;
    generating data channels corresponding to each of the tissue sites based on the sensor signals;
    calculating signal quality for each of the data channels using one or more processors of the physiological monitor;
    outputting a first oxygen status parameter or plethysmograph derived from at least one of the data channels based upon a comparison of the calculated signal qualities;
    ignoring a noisy one of the data channels based upon the calculated signal qualities; and
    deriving the oxygen status parameter from one or more of the remaining data channels during a particular time period.

* * * * *

UNITED STATES PATENT AND TRADEMARK OFFICE
CERTIFICATE OF CORRECTION

PATENT NO. : 7,899,507 B2  Page 1 of 1
APPLICATION NO. : 11/417545
DATED : March 1, 2011
INVENTOR(S) : Ammar Al-Ali et al.

It is certified that error appears in the above-identified patent and that said Letters Patent is hereby corrected as shown below:

In the Specifications:

At Column 11, Line 42 (Approx.), change "$f_0'$," to --$f_0$,--.

At Column 12, Line 13, change "$Sp_aO_2$" to --$Sp_vO_2$--.

At Column 12, Line 58, change ".$\mu_b$" to --$\mu_b$--.

At Column 12, Line 59, change ".$\mu_t$" to --$\mu_t$--.

At Column 12, Line 61, change ".$\mu_t$," to --$\mu_t$,--.

At Column 13, Line 1, change "$\epsilon_{Hb,\epsilon}$" to --$\epsilon_{Hb,\lambda}$--.

At Column 13, Line 3, change ".$\mu_b$," to --$\mu_b$,--.

At Column 13, Line 36 (Approx.), change "$RD(\omega)$." to --$IR(\omega)$.--.

At Column 19, Line 15, change "$Sp_aO_2$" to --$Sp_vO_2$--.

At Column 22, Line 64, change ".$\Delta pleth_{xy}$" to --$\Delta pleth_{xy}$--.

In the Claims:

At Column 23, Line 33, in Claim 1, after "portion" insert --of--.

Signed and Sealed this
Sixteenth Day of October, 2012

David J. Kappos
*Director of the United States Patent and Trademark Office*

(12) EX PARTE REEXAMINATION CERTIFICATE (9458th)
United States Patent
Al-Ali et al.

(10) Number: US 7,899,507 C1
(45) Certificate Issued: Dec. 26, 2012

(54) PHYSIOLOGICAL MONITOR

(76) Inventors: Ammar Al-Ali, Costa Mesa, CA (US);
Mohamed K. Diab, Mission Viejo, CA (US); Massi E. Kiani, Laguna Niguel, CA (US); Robert James Kopotic, Jamul, CA (US); David Tobler, Westminster, CO (US)

Reexamination Request:
No. 90/012,541, Sep. 14, 2012

Reexamination Certificate for:
Patent No.: 7,899,507
Issued: Mar. 1, 2011
Appl. No.: 11/417,545
Filed: May 3, 2006

Certificate of Correction issued Oct. 16, 2012.

Related U.S. Application Data

(63) Continuation of application No. 11/104,720, filed on Apr. 13, 2005, now Pat. No. 7,761,128, which is a continuation of application No. 10/668,487, filed on Sep. 22, 2003, now Pat. No. 6,898,452, which is a continuation of application No. 10/026,013, filed on Dec. 21, 2001, now Pat. No. 6,714,804, which is a continuation of application No. 09/323,176, filed on May 27, 1999, now Pat. No. 6,334,065.

(60) Provisional application No. 60/087,802, filed on Jun. 3, 1998.

(51) Int. Cl.
*A61B 5/1455* (2006.01)

(52) U.S. Cl. .................................. 600/323; 600/340
(58) Field of Classification Search ...................... None
See application file for complete search history.

(56) References Cited

To view the complete listing of prior art documents cited during the proceeding for Reexamination Control Number 90/012,541, please refer to the USPTO's public Patent Application Information Retrieval (PAIR) system under the Display References tab.

*Primary Examiner* — Robert Nasser

(57) ABSTRACT

A patient monitor has multiple sensors adapted to attach to tissue sites of a living subject. The sensors generate sensor signals that are responsive to at least two wavelengths of optical radiation after attenuation by pulsatile blood within the tissue sites. Multiple data channels and associated quality parameters are derived from the sensor signals. A processor is configured to operate on the channels according to the quality parameters so as to provide a robust oxygen status measurement.

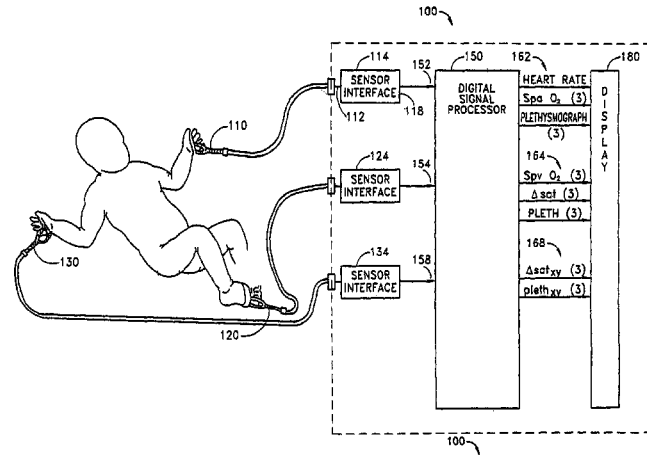

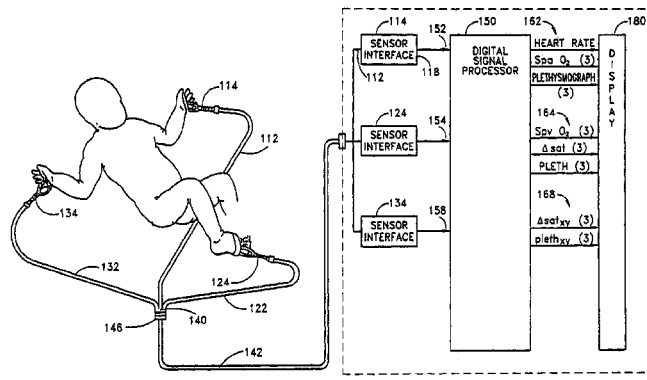

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 11 is confirmed.

Claims 2-10 were not reexamined.

\* \* \* \* \*